(12) United States Patent
Schultz et al.

(10) Patent No.: US 7,955,318 B1
(45) Date of Patent: Jun. 7, 2011

(54) MULTIPURPOSE LARGE BORE MEDICAL SUCTION SYSTEMS

(76) Inventors: Joseph P. Schultz, Atlanta, GA (US); Steven J. Lipsky, Paradise Valley, AZ (US)

( * ) Notice: Subject to any disclaimer, the term of this patent is extended or adjusted under 35 U.S.C. 154(b) by 1446 days.

(21) Appl. No.: 11/179,690

(22) Filed: Jul. 11, 2005

Related U.S. Application Data

(60) Provisional application No. 60/588,717, filed on Jul. 16, 2004.

(51) Int. Cl.
*A61M 1/00* (2006.01)
*A61M 27/00* (2006.01)
(52) U.S. Cl. .................... 604/540; 604/319; 604/541
(58) Field of Classification Search .............. 604/317, 604/319, 118, 119, 540, 542; 600/573, 579, 600/581
See application file for complete search history.

(56) References Cited

U.S. PATENT DOCUMENTS

| | | | |
|---|---|---|---|
| 4,490,138 A | 12/1984 | Lipsky et al. | |
| 5,921,970 A * | 7/1999 | Vandenberg | 604/264 |
| 6,045,516 A * | 4/2000 | Phelan | 600/579 |
| 6,279,574 B1 * | 8/2001 | Richardson et al. | 128/204.18 |

* cited by examiner

*Primary Examiner* — Melanie J Hand
(74) *Attorney, Agent, or Firm* — Stoneman Law Patent Group; Martin L. Stoneman

(57) ABSTRACT

A multipurpose large bore medical suction system relating to medical instruments comprising suction devices that are used to remove material from body cavities during medical procedures, such as, for example, during cardiopulmonary resuscitation or trauma stabilization. The system is designed to adapt to large-bore medical vacuum sources such as the large-bore port of a collection canister. The system comprises a series of interchangeable tips including a means for endotracheal-catheter suctioning.

15 Claims, 10 Drawing Sheets

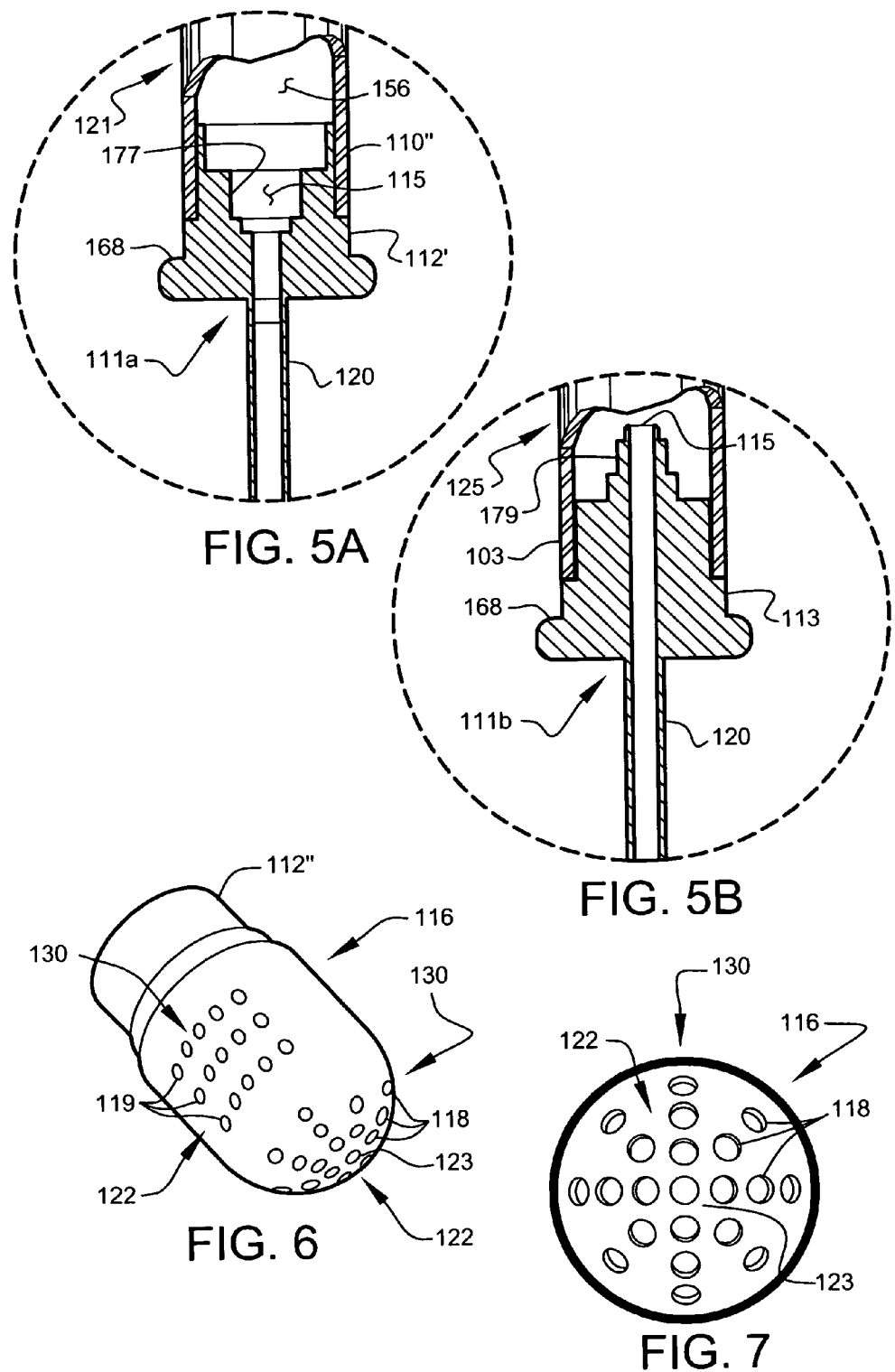

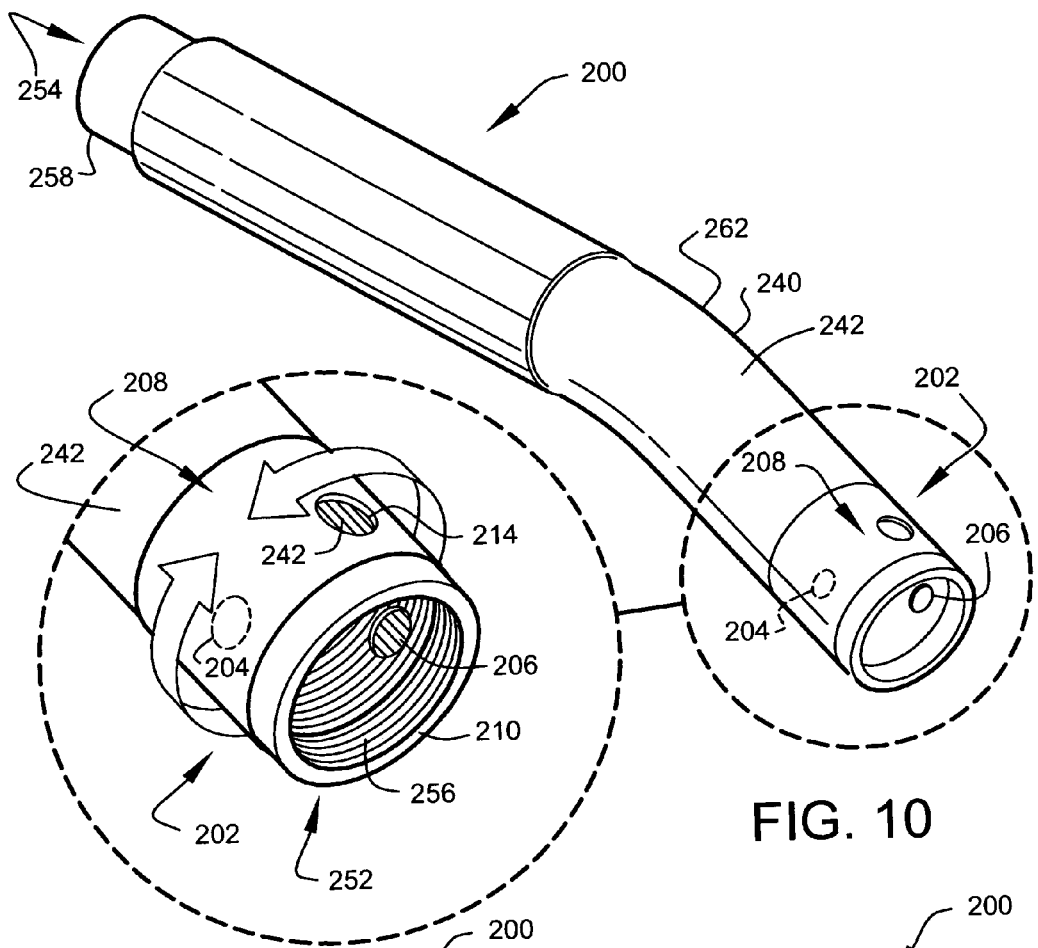
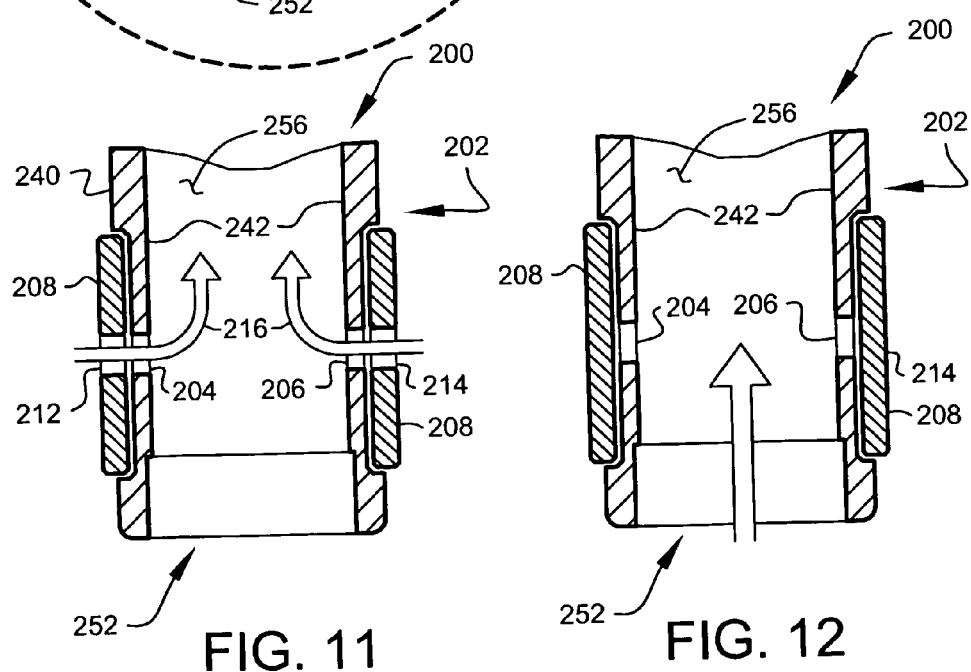
FIG. 10
FIG. 11  FIG. 12

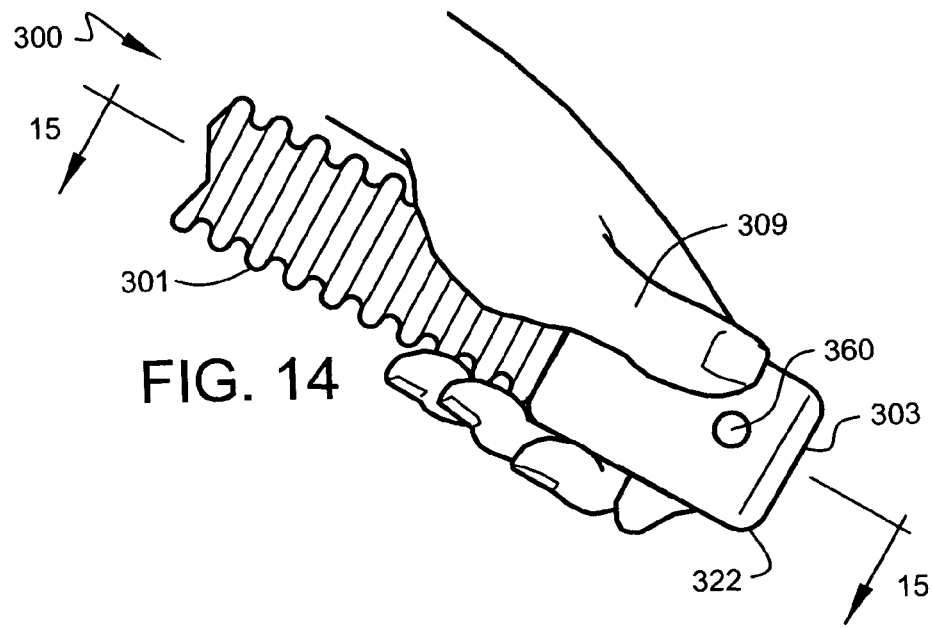
FIG. 14
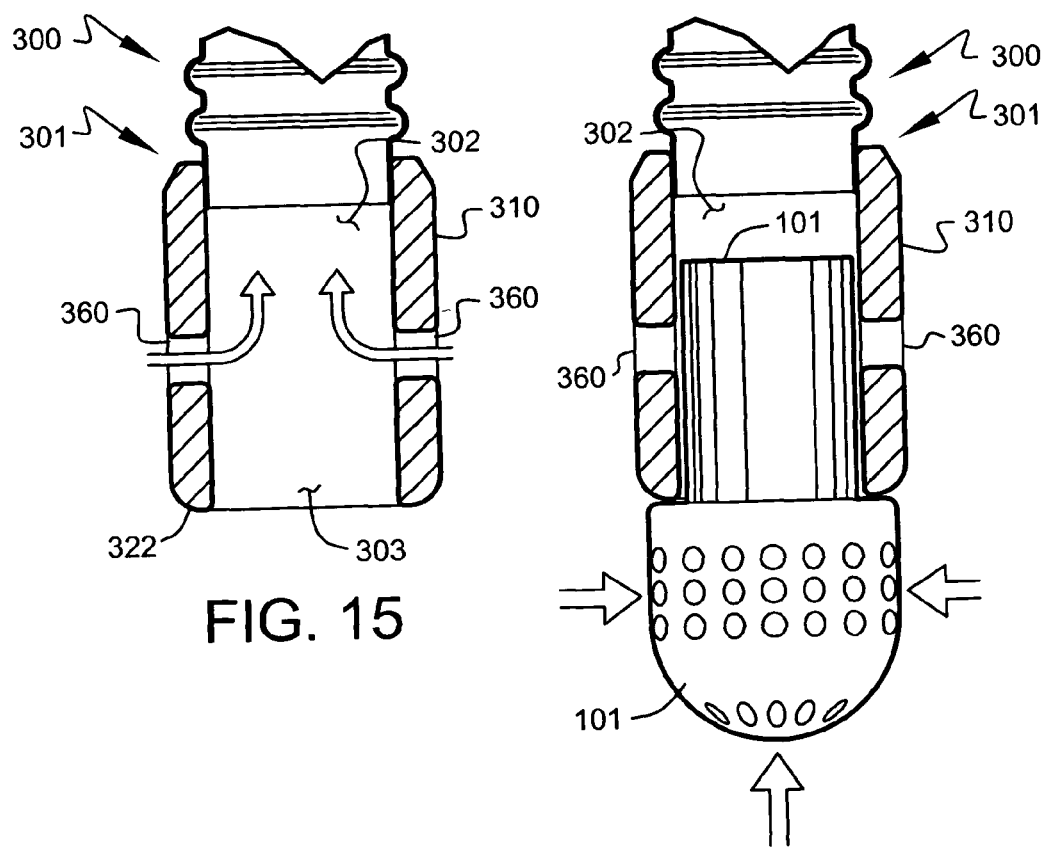
FIG. 15
FIG. 16

MULTIPURPOSE LARGE BORE MEDICAL SUCTION SYSTEMS

CROSS-REFERENCE TO RELATED APPLICATION

The present application is related to and claims priority from prior provisional application Ser. No. 60/588,717, filed Jul. 16, 2004, entitled "MULTIPURPOSE LARGE BORE MEDICAL SUCTION SYSTEM WITH NARROW BORE SUCTION COMPONENT", the contents of which is incorporated herein by this reference and is not admitted to be prior art with respect to the present invention by the mention in this cross-reference section.

BACKGROUND

This invention relates to providing multipurpose large bore medical suction systems. More particularly this invention relates to medical instruments comprising suction devices that are used to remove material from body cavities during medical procedures, such as, for example, during cardiopulmonary resuscitation or trauma stabilization.

Many medical procedures require the evacuation and collection of bodily tissues and fluids. For example, during cardiac arrest a patient's stomach contents may be regurgitated and fill the hypopharyngeal, oropharyngeal, nasopharyngeal, and oral cavities. Before effective resuscitation can be accomplished, the patient's throat must be cleared of foreign matter to allow establishment of an open airway. Often this clearing of the throat includes removal of vomitus comprising large pieces of poorly chewed and undigested food. Commonly, the clinician will remove material having a size of ½ inch in diameter or larger.

Once the patient's throat is cleared, an artificial airway can be established by the clinician via endotracheal placement of an endotracheal tube (ETT). After insertion of the ETT, it is usually necessary to periodically suction the interior of the ETT to clear any lung secretions or aspirated material that might obstruct the desired gas exchange through the ETT. Currently, it is necessary to use a small-bore suction-catheter that can be inserted and slid down the ETT to accomplish this procedure.

Presently, no single medical device exists that quickly converts from large volume/size material removal, during procedures such as cardiopulmonary resuscitation or trauma stabilization, to small-bore catheter-type suctioning, during procedures such as the maintenance of an ETT. Such a versatile and quickly convertible system would, during many emergencies, reduced the time required to transition between patient suctioning procedures, thus increasing the likelihood of a successful medical outcome.

OBJECTS AND FEATURES OF THE INVENTION

A primary object and feature of the present invention is to provide a system to overcome the above-described problems.

It is a further object and feature of the present invention to provide such a system especially suited for multipurpose use including narrow-bore suctioning during cardiopulmonary resuscitation, trauma stabilization, toxic ingestions, surgery and similar medical procedures.

It is another object and feature of the present invention to provide such a system that resists clogging and that can be adapted for narrow-bore suctioning.

It is a further object and feature of the present invention to provide such a system having multiple tip-adaptors for connection to the inlet-end of a large-bore suction device that can be selectively chosen for different suction functions.

It is another object and feature of the present invention to provide such a system providing a small-bore suction system device that may be used with large-bore suction devices or large bore-vacuum apparatus.

It is a further object and feature of the present invention to provide such a system having a narrow-bore suction adapter for a large-bore suction system that can be removed without significantly affecting the overall length or curvature properties of the large bore suction system.

It is yet a further object and feature of the present invention to provide such a system having multiple types of adapters for use when changing from the large bore needs of an oropharyngeal clearance during trauma resuscitation to small-bore flexible suctioning of the ETT tube during the post intubation phase of the resuscitation.

A further primary object and feature of the present invention is to provide such a system that is efficient, inexpensive, and handy. Other objects and features of this invention will become apparent with reference to the following descriptions.

SUMMARY OF THE INVENTION

In accordance with a preferred embodiment hereof, this invention provides a system relating to multipurpose large-bore medical suction systems, compatible with at least one large-bore suction conduit comprising at least one distal inlet and at least one proximal outlet, wherein such at least one proximal outlet is connectable to at least one large-bore port of at least one collection canister, wherein such at least one distal inlet comprises at least one large inlet-bore-diameter no larger than about the large inlet-bore-diameter of the at least one large-bore port, and wherein such at least one distal inlet is adapted to allow fluid communication with such at least one large-bore port, such system comprising: at least one narrow-bore conduit adapted to pass at least one pressurized fluid; and at least one large-bore adapter structured and arranged to adapt such at least one narrow-bore conduit to the at least one distal inlet of the at least one large-bore suction conduit; wherein such at least one narrow-bore conduit comprises a sufficient length and flexibility to allow entry of such at least one narrow-bore conduit into at least one endotracheal tube to allow tracheal suctioning.

Moreover, it provides such a system wherein: such at least one large-bore adapter comprises at least one first coupler adapted to removably couple such at least one narrow-bore conduit to the at least one distal inlet of the at least one large-bore suction conduit; and such at least one first coupler is structured and arranged to form at least one pressure-resisting seal with such at least one distal inlet. Additionally, it provides such a system wherein: such at least one narrow-bore conduit comprises at least one distal-end portion, and at least one proximal-end portion; such at least one proximal-end portion comprises such at least one first coupler; and such at least one distal-end portion comprises at least one inlet end aperture. And, it provides such a system wherein such at least one first coupler is adapted to removably couple to at least one first one and at least one second one of such at least one large-bore suction conduits; and such at least one first one comprises at least one end bore-diameter larger that that of such at least one second one.

Also, it provides such a system wherein such at least one large-bore suction conduit comprises at least one bore-diameter larger than about ¼ inch. In addition, it provides such a system wherein such at least one first coupler is adapted to removably couple to at least one vacuum source comprising at least one about-15 millimeter-diameter coupling member. And, it provides such a system wherein such at least one first coupler is adapted to removably couple to at least one vacuum source comprising at least one about-22 millimeter-diameter coupling member. Further, it provides such a system wherein such at least one narrow-bore conduit comprises at least one narrow-bore tracheal suction catheter adapted to assist deep endotracheal tube tracheal suctioning.

Even further, it provides such a system wherein such at least one distal end further comprises at least one pressure-relieving side-aperture adapted to assist in relieving fluid pressure at such at least one inlet end-aperture. Moreover, it provides such a system wherein such at least one large-bore adapter further comprises at least one pressure regulator adapted to regulate at least one level of fluid pressure within such at least one narrow-bore passage. Additionally, it provides such a system wherein such at least one pressure regulator comprises at least one aperture valve adapted to allow thumb-controlled regulation of the at least one level of fluid pressure within such at least one narrow-bore passage.

Also, it provides such a system further comprising: at least one blunt-tip adapter structured and arranged to assist in providing blunt-tip suctioning of medical materials; wherein such at least one blunt-tip adapter comprises at least one blunt-tip proximal-end outlet and at least one blunt-tip distal-end inlet region; wherein such at least one blunt-tip distal-end inlet region comprises a plurality of narrow-bore inlets; and wherein such at least one blunt-tip adapter comprises at least one second coupler adapted to removably couple such at least one blunt-tip proximal-end outlet to the at least one distal inlet of the at least one large-bore suction conduit. And, it provides such a system wherein such at least one second coupler is adapted to removably couple to at least one first one and at least one second one of such at least one large-bore suction conduits; and such at least one first one comprises at least one end bore-diameter larger that that of such at least one second one.

In addition, it provides such a system further comprising at least one large-bore hand wand adapter structured and arranged to allow large-bore hand-wand manipulation of such at least one narrow-bore conduit. And, it provides such a system further comprising at least one large-bore hand wand adapter structured and arranged to allow large-bore hand-wand manipulation of such at least one narrow-bore passage.

Further, it provides such a system wherein such large-bore hand wand adapter comprises: at least one distal fluid-inlet; at least one proximal fluid-outlet; at least one large bore inner passageway situate between such at least one distal fluid-inlet and such at least one proximal fluid-outlet; and at least one aperture valve adapted to allow manually-controlled regulation of at least one level of fluid pressure within such at least one large bore inner passageway; wherein such at least one distal fluid-inlet is adapted to couple with such at least one first coupler.

Even further, it provides such a system wherein such at least one proximal fluid-outlet comprises at least one third coupler adapted to removably couple such at least one proximal fluid-outlet to such at least one large-bore suction conduit. Moreover, it provides such a system wherein such at least one third coupler is adapted to removably couple to at least one vacuum source comprising at least one bore diameter larger than about ¼ inch. Additionally, it provides such a system wherein such at least one third coupler is adapted to removably couple to at least one vacuum source comprising at least one about-15 millimeter-diameter coupling member.

Also, it provides such a system wherein such at least one third coupler is adapted to removably couple to at least one vacuum source comprising at least one about-22 millimeter-diameter coupling member. In addition, it provides such a system wherein such at least one distal fluid-inlet is adapted to removably couple to at least one vacuum source comprising at least one about-15 millimeter-diameter coupling member. And, it provides such a system wherein such at least one distal fluid-inlet is adapted to removably couple to at least one vacuum source comprising at least one about-22 millimeter-diameter coupling member.

Further, it provides such a system wherein such at least one aperture valve comprises: at least one first aperture adapted to provide fluid pressure communication between such at least one large bore inner passageway and at least one other ambient fluid pressure external of such large-bore hand wand adapter; and at least one adjustable occluder adapted to adjustably occlude such at least one first aperture between about un-occluded and about fully-occluded; wherein such adjustable occluding by such at least such at least one adjustable occluder is manually controllable by at least one user.

Even further, it provides such a system wherein: such at least one large bore inner passageway comprises at least one hollow cylindrical outer wall; such at least one adjustable occluder comprises at least one hollow cylindrical ring coaxially disposed about such at least one hollow cylindrical outer wall; such at least one hollow cylindrical ring is rotatable relative to such at least one hollow cylindrical outer wall; such at least one hollow cylindrical ring comprises at least one second aperture adapted to provide fluid pressure communication between such at least one first aperture and such at least one other ambient fluid pressure external of such large-bore hand wand adapter; such at least one second aperture is at least partially alignable with such at least one first aperture by rotational adjustment of such at least one hollow cylindrical ring; and such at least partial alignment of such at least one second aperture with such at least one first aperture allows such fluid pressure communication between such at least one large bore inner passageway and such at least one other ambient fluid pressure external of such large-bore hand wand adapter.

Moreover, it provides such a system wherein such at least one large bore inner passageway comprises at least two non-congruent longitudinal axes. Additionally, it provides such a system further comprising such at least one large-bore suction conduit. Also, it provides such a system further comprising such at least one large-bore suction conduit. In addition, it provides such a system wherein: such at least one large-bore suction conduit comprises at least one distal inlet and at least one proximal outlet; such at least one proximal outlet is adapted to couple to the at least one large-bore port of the at least one collection canister; wherein such at least one distal inlet comprises at least one large inlet-bore-diameter substantially matching the inlet bore-diameter of the at least one large-bore port; and wherein such at least one proximal outlet is structured and arranged to allow fluid communication between such at least one large-bore port and such at least one distal inlet.

In accordance with another preferred embodiment hereof, this invention provides a kit system relating to multipurpose large-bore medical suction systems, compatible with at least one large-bore suction conduit comprising at least one distal inlet and at least one proximal outlet, wherein such at least one proximal outlet is connectable to at least one large-bore port of at least one collection canister, wherein such at least one distal inlet comprises at least one large inlet-bore-diameter no larger than about the large inlet-bore-diameter of the at least one large-bore port, and wherein such at least one distal inlet is adapted to allow fluid communication with such at least one large-bore port, such kit system comprising: at least one narrow-bore tracheal suction catheter comprising a sufficient length and flexibility to allow entry of such at least one narrow-bore conduit into at least one endotracheal tube to allow tracheal suctioning; and at least one blunt-tip adapter structured and arranged to allow large-bore suctioning of medical materials; wherein such at least one narrow-bore tracheal suction catheter comprises, at least one large-bore adapter structured and arranged to adapt such at least one narrow-bore tracheal suction catheter to the at least one distal inlet of the at least one large-bore suction conduit, and such at least one large-bore adapter comprises at least one first coupler adapted to removably couple such at least one narrow-bore conduit to the at least one distal inlet of the at least one large-bore suction conduit; and wherein such least one blunt-tip adapter comprises at least one blunt-tip proximal-end outlet and at least one blunt-tip distal-end inlet region, wherein such at least one blunt-tip distal-end inlet region comprises a plurality of narrow-bore inlets, and wherein such at least one blunt-tip adapter comprises at least one second coupler adapted to removably couple such at least one blunt-tip proximal-end outlet to the at least one distal inlet of the at least one large-bore suction conduit.

And, it provides such a kit system further comprising: at least one large-bore hand wand adapter; wherein such at least one large-bore hand wand adapter comprises at least one distal fluid-inlet, at least one proximal fluid-outlet, at least one large bore inner passageway situate between such at least one distal fluid-inlet and such at least one proximal fluid-outlet, and at least one aperture valve adapted to allow manually-controlled regulation of at least one level of fluid pressure within such at least one large bore inner passageway; wherein such at least one proximal fluid-outlet comprises at least one third coupler adapted to removably couple such at least one proximal fluid-outlet to the at least one distal inlet of the at least one large-bore suction conduit; and wherein such at least one distal fluid-inlet is adapted to couple with such at least one first coupler.

Further, it provides such a kit system further comprising: such at least one large-bore suction conduit; wherein such at least one large-bore suction conduit comprises at least one distal inlet and at least one proximal outlet; wherein such at least one proximal outlet is adapted to couple to the at least one large-bore port of the at least one collection canister; wherein such at least one distal inlet comprises at least one large inlet-bore-diameter substantially matching the inlet bore-diameter of the at least one large-bore port; and wherein such at least one proximal outlet is structured and arranged to allow fluid communication between such at least one large-bore port and such at least one distal inlet. Even further, it provides such a kit system further comprising at least one package adapted to enclose components of such kit system.

In accordance with another preferred embodiment hereof, this invention provides a system relating to multipurpose large-bore medical suction systems, compatible with at least one large-bore suction conduit comprising at least one distal inlet and at least one proximal outlet, wherein such at least one proximal outlet is connectable to at least one large-bore port of at least one collection canister, wherein such at least one distal inlet comprises at least one large inlet-bore-diameter no larger than about the large inlet-bore-diameter of the at least one large-bore port, and wherein such at least one distal inlet is adapted to allow fluid communication with such at least one large-bore port, such system comprising: at least one narrow-bore catheter adapted to convey vacuum pressure; and at least one large-bore adapter structured and arranged to adapt such at least one narrow-bore catheter to the at least one distal inlet of the at least one large-bore suction conduit; wherein such at least one narrow-bore catheter comprises a sufficient length and flexibility to allow entry of such at least one narrow-bore conduit into at least one endotracheal tube to allow tracheal suctioning. Moreover, it provides such a system wherein: such at least one large-bore adapter comprises at least one first coupler adapted to removably couple such at least one narrow-bore catheter to the at least one distal inlet of the at least one large-bore suction conduit; such at least one narrow-bore catheter comprises at least one distal-end portion, and at least one proximal-end portion; such at least one proximal-end portion comprises such at least one first coupler; and such at least one distal-end portion comprises at least one inlet end-aperture.

Additionally, it provides such a system wherein such at least one first coupler is adapted to removably couple to at least one vacuum source comprising at least one bore diameter larger than about ¼ inch. Also, it provides such a system wherein such at least one first coupler is adapted to removably couple to at least one respiratory adapter comprising at least one bore diameter of between about 10 millimeters and about 30 millimeters.

In accordance with another preferred embodiment hereof, this invention provides a system relating to large-bore medical suction systems comprising: at least one blunt-tip adapter structured and arranged to allow large-bore suctioning of medical materials; wherein such at least one blunt-tip adapter comprises at least one blunt-tip proximal-end outlet and at least one blunt-tip distal-end inlet region; wherein such at least one blunt-tip distal-end inlet region comprises at least six narrow-bore inlets; and wherein such at least one blunt-tip adapter comprises at least one blunt-tip coupler adapted to removably couple such at least one blunt-tip proximal-end outlet to at least one large-bore suction conduit.

In addition, it provides such a tip system wherein such at least one large-bore suction conduit comprises at least one bore-diameter larger than about ¼ inch. And, it provides such a tip system wherein such at least one blunt-tip coupler is adapted to removably couple to at least one vacuum source comprising at least one about-15 millimeter-diameter coupling member. Further, it provides such a tip system wherein such at least one blunt-tip coupler is adapted to removably couple to at least one vacuum source comprising at least one about-22 millimeter-diameter coupling member. Even further, it provides such a tip system wherein each of such narrow-bore inlets comprises an aperture diameter of between about one-half millimeter and about five millimeters.

In accordance with another preferred embodiment hereof, this invention provides a system relating to large-bore medical suction wands comprising: at least one large-bore hand wand adapter structured and arranged to allow large-bore hand-wand manipulation of such at least one narrow-bore passage; wherein such large-bore hand wand adapter comprises at least one distal fluid-inlet; at least one proximal fluid-outlet; at least one large bore inner passageway situate between such at least one distal fluid-inlet and such at least one proximal fluid-outlet; and at least one aperture valve adapted to allow manually-controlled regulation of at least one level of fluid pressure within such at least one large bore inner passageway; wherein such at least one proximal fluid-outlet comprises at least one wand-outlet coupler adapted to removably couple such at least one proximal fluid-outlet to at least one large-bore suction conduit; and wherein such at least one aperture valve comprises at least one first aperture adapted to provide fluid pressure communication between such at least one large bore inner passageway and at least one other ambient fluid pressure external of such large-bore hand wand adapter, and at least one adjustable occluder adapted to adjustably occlude such at least one first aperture between about un-occluded and about fully-occluded, wherein such adjustable occluding by such at least such at least one adjustable occluder is manually controllable by at least one user.

Even further, it provides such a system wherein: such at least one large bore inner passageway comprises at least one hollow cylindrical outer wall; such at least one adjustable occluder comprises at least one hollow cylindrical ring coaxially disposed about such at least one hollow cylindrical outer wall; such at least one hollow cylindrical ring is rotatable relative to such at least one hollow cylindrical outer wall; such at least one hollow cylindrical ring comprises at least one second aperture adapted to provide fluid pressure communication between such at least one first aperture and such at least one other ambient fluid pressure external of such large-bore hand wand adapter; such at least one second aperture is at least partially alignable with such at least one first aperture by rotational adjustment of such at least one hollow cylindrical ring; and such at least partial alignment of such at least one second aperture with such at least one first aperture allows such fluid pressure communication between such at least one large bore inner passageway and such at least one other ambient fluid pressure external of such large-bore hand wand adapter.

Even further, it provides such a system wherein such at least one wand-outlet coupler is adapted to removably couple to at least one vacuum source comprising at least one bore diameter larger than about ¼ inch. Even further, it provides such a system wherein such at least one wand-outlet coupler is adapted to removably couple to at least one vacuum source comprising at least one about-15 millimeter-diameter coupling member. Even further, it provides such a system wherein such at least one wand-outlet coupler is adapted to removably couple to at least one vacuum source comprising at least one about-22 millimeter-diameter coupling member.

Even further, it provides such a system wherein such at least one distal fluid-inlet is adapted to removably couple to at least one about-15 millimeter-diameter coupling member. Even further, it provides such a system wherein such at least one distal fluid-inlet is adapted to removably couple to at least one about-22 millimeter-diameter coupling member.

In accordance with another preferred embodiment hereof, this invention provides a system relating to multipurpose large-bore medical suction systems connectable to at least one large-bore port of at least one medical collection canister comprising: at least one substantially flexible large-bore suction conduit comprising at least one distal inlet, at least one proximal outlet, and at least one fluid channel adapted to channel at least one fluid between such at least one distal inlet and such at least one proximal outlet; wherein such at least one proximal outlet is connectable to the at least one large-bore port of the at least one medical collection canister; wherein such at least one distal inlet comprises at least one large inlet-bore-diameter no larger than about the large inlet-bore-diameter of the at least one large-bore port; wherein such at least one fluid channel comprises at least one pressure-regulating aperture adapted to assist in providing pressure regulation of at least one level of fluid pressure within such at least one fluid channel. Additionally, it provides such a system wherein: such at least one distal inlet comprises at least one tip coupler adapted to couple at least one medical tip device to such at least one distal inlet; and such at least one pressure-regulating aperture is structured and arranged to be substantially occluded by such coupling of such at least one medical tip device to such at least one tip coupler. Furthermore, it provides such a system wherein such at least one tip coupler comprises at least one atraumatic shape adapted to reduce tissue trauma during at least one medical suctioning procedure using such at least one tip coupler; and such at least one atraumatic shape comprises at least one substantially rounded surface. Even further, it provides such a system wherein such at least one tip coupler comprises at least one substantially resilient material adapted to reduce tissue trauma during at least one medical suctioning procedure using such at least one tip coupler.

Furthermore, it provides such a system wherein such at least one pressure-regulating aperture is structured and arranged to be manually operable by at least one hand of at least one user.

BRIEF DESCRIPTION OF THE DRAWINGS

FIG. 5A shows a side view, in partial section, of the narrow-bore suction component coupled to a large-bore hand wand.

FIG. 5B shows a side view, in partial section, of an alternate narrow-bore suction component coupled to the distal inlet of a large-bore suction conduit.

FIG. 6 shows a perspective view illustrating a large-bore blunt-tip component of the multipurpose large-bore medical suction system according to a preferred embodiment of the present invention.

FIG. 7 shows an end view illustrating a preferred aperture pattern of the large-bore blunt-tip component of FIG. 6

FIG. 10 shows perspective views of an alternate suction wand comprising a rotatable vacuum modulator according to preferred embodiment of the present invention.

FIG. 11 shows a partial side view, of a cut-away section, of the alternate suction wand of FIG. 10.

FIG. 12 shows a partial side view, of a cut-away section, of the alternate suction wand of FIG. 10.

FIG. 14 shows a side view illustrating the alternate large-bore medical suction system in use according to the preferred embodiment of FIG. 13.

FIG. 15 shows a sectional view through the section 15-15 of FIG. 14 illustrating the alternate multipurpose large-bore medical suction system without an installed tip.

FIG. 16 shows a sectional view aligned with section 15-15 of FIG. 14 illustrating the alternate multipurpose large-bore medical suction system with an installed tip.

DETAILED DESCRIPTION OF THE BEST MODES AND PREFERRED EMBODIMENTS OF THE INVENTION

Figure 1:
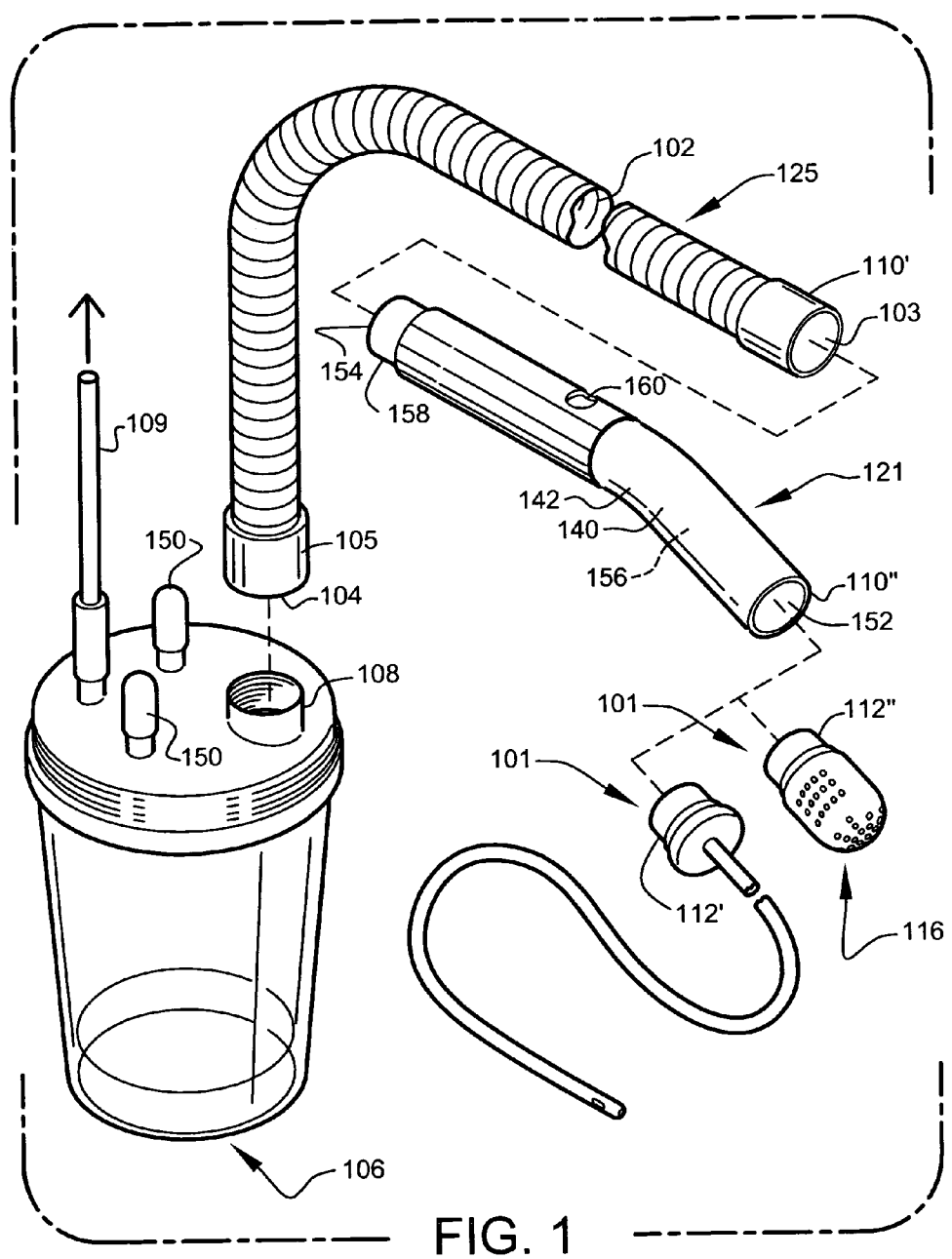
FIG. 1 shows an exploded view of a multipurpose large-bore medical suction system according to preferred embodiments of the present invention.
Figure 2:
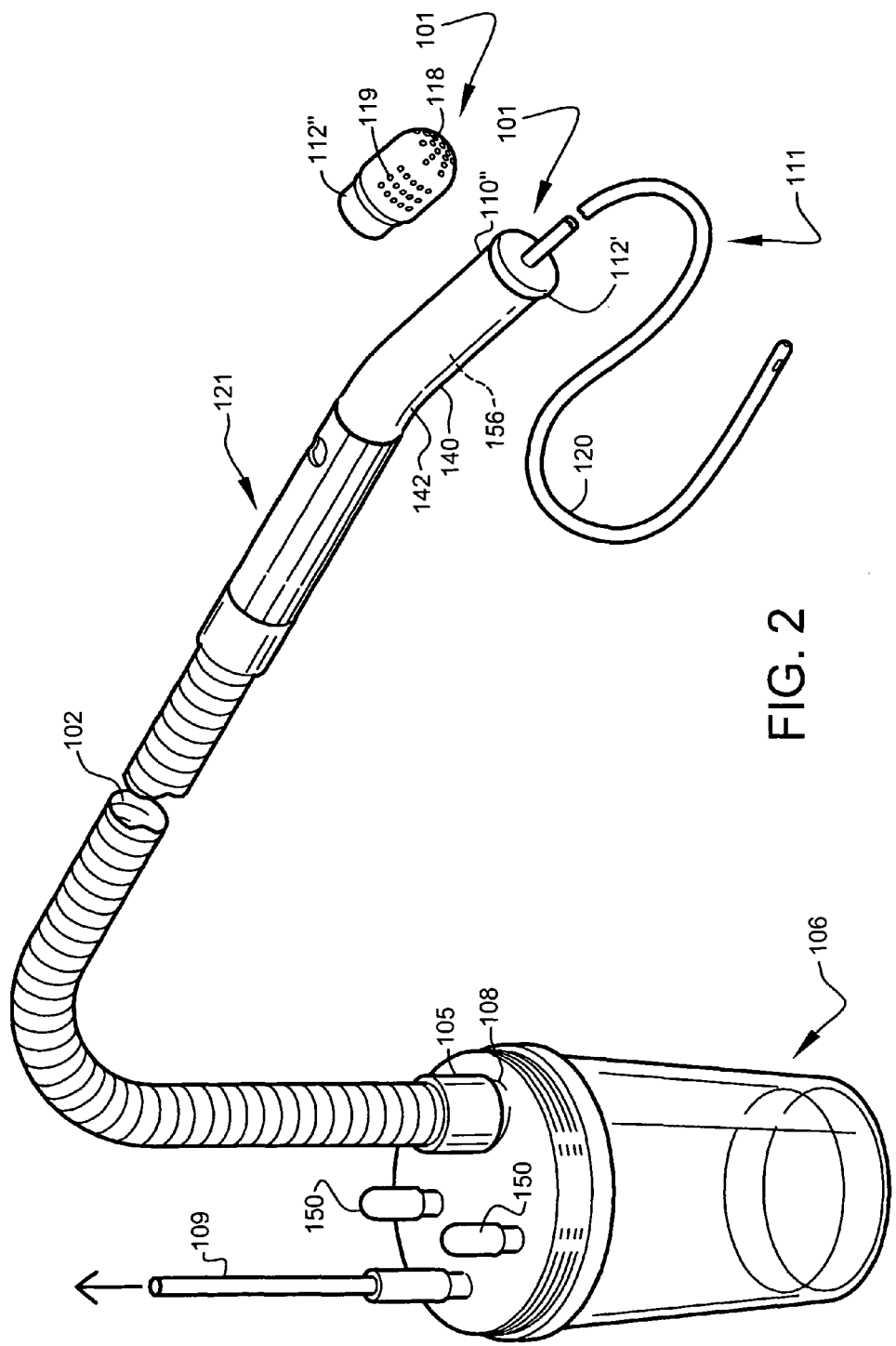
FIG. 2 shows a perspective view illustrating an assembled multipurpose large-bore medical suction system according to a preferred embodiment of FIG. 1.

FIG. 1 shows an exploded view of multipurpose large-bore medical suction system 100 according to preferred embodiments of the present invention. FIG. 2 shows a perspective view illustrating an assembled multipurpose large-bore medical suction system 100 according to a preferred embodiment of FIG. 1. Referring now to FIG. 1 and FIG. 2, multipurpose large-bore medical suction system 100 preferably comprises a modular system of medical suction devices. Each device preferably comprises an inter-compatible connection format adapted to allow individual components of multipurpose large-bore medical suction system 100 to be quickly interchangeable. Preferred embodiments of multipurpose large-bore medical suction system 100 preferably range from a single suction adapter tip 101 to a complete large-bore medical suction kit (see FIG. 8A and FIG. 8B) comprising one or more suction adapter tips 101, large-bore hand wand adapter 121, and large-bore suction conduit 125.

Preferably, each preferred embodiment of large-bore medical suction system 100 comprises a component, or group of components, adapted to couple with at least one large-bore suction conduit or large-bore vacuum port of at least one medical vacuum device. For example, large-bore medical suction system 100 is preferably adapted to utilize large-bore inlet opening 108 of a medical collection canister 106.

Medical collection canisters, such as medical collection canister 106, typically comprise several narrow-bore vacuum ports 150 and at least one large-bore inlet opening 108, as shown. Large-bore inlet opening 108 may comprise, for example, a pour spout or similar large-diameter aperture of the canister. Under present practices, the term "small-bore" comprises bore diameters equal to or less than ¼ inch. It should be noted that, in the present disclosure, the term "large bore" shall be defined to include a broad range of medical connectors and connector bore sizes comprising diameters greater than about ¼ inch, and preferably including 15 millimeter (mm) and 22 millimeter (mm) medical conduit connections.

During operation, the interior of medical collection canister 106 is configured to be in fluid communication with at least one mechanical vacuum source, illustrated in FIG. 1 as vacuum supply conduit 109. Typically, each of the canister vacuum ports is in fluid communication with the interior of medical collection canister 106. Thus, during operation, a negative fluid pressure generated within medical collection canister 106 is present and functionally accessible at each of the canister vacuum ports, including at large-bore inlet opening 108. In general, each of the preferred interchangeable components of large-bore medical suction system 100 are preferably adapted to utilize, at least in part, such negative fluid pressure (vacuum) present at large-bore inlet opening 108, as shown.

Preferably providing a single large-bore suction system having multiple types of suction adapters is highly beneficial when changing needs arise during a surgical procedure. For example, a medical practitioner may need to remove a large blood clot from a patient's abdomen, during an open laporotomy, using a large bore suction instrument comprising large suction openings. During the same surgery, the medical practitioner may need to quickly changeover to a small-bore aspiration device comprising fine atraumatic holes, to permit, for example, suctioning of fluids around the delicate intestines.

Large-bore medical suction system 100 is preferably adapted to accommodate both procedures by eliminating the requirement to set up multiple, and substantially redundant, suctioning systems. The inherent versatility of large-bore medical suction system 100 reduces the amount of time and money required to properly equip an operating space, greatly reduces the distraction of switching between large and small bore suctioning during a procedure, and significantly reduces the workload of personnel currently responsible for such redundant device-swapping tasks.

Preferably, large-bore suction conduit 125 of large bore medical suction system 100 comprises large bore inner passageway 102 situate between distal inlet 103 and proximal outlet 104, as shown. Preferably, large-bore suction conduit 125 further comprises large-bore proximal-end outlet-coupling 105 adapted to form an airtight coupling seal with large-bore inlet opening 108, as shown. The opposing end of large-bore suction conduit 125 preferably comprises large-bore distal-end inlet-coupling 110', as shown. Preferably, large-bore distal-end inlet-coupling 110' comprises a physical configuration substantially matching that of a large-bore medical connector. Most preferably, large-bore distal-end inlet coupling 110' of large-bore suction conduit 125 is physically configured to removably connect with 15 mm respiratory coupling members and/or 22 mm respiratory coupling members. Upon reading the teachings of this specification, those of ordinary skill in the art will now understand that, under appropriate circumstances, considering such issues as user preference, intended use, etc., other connector formats, such as proprietary configurations, instrument specific adapters, alternate handing of male and female connector ends, etc., may suffice.

Preferably, distal inlet 103 of large-bore suction conduit 125 comprises a large inlet-bore-diameter substantially matching the large inlet-bore-diameter of large-bore inlet opening 108. Upon reading the teachings of this specification, those with ordinary skill in the art will now understand that, under appropriate circumstances, considering issues such as intended use, procedure requirements, etc., other bore sizing, such as, for example, transitioning between large bore diameters and smaller bore diameters, etc., may suffice. Preferably, the inner diameter of large bore inner passageway 102 is sized to substantially match the large inlet-bore-diameter of large-bore inlet opening 108. Preferably, the inner diameter of large bore inner passageway 102 comprises a measurement that is not less than about ¼ inch. More preferably, large bore inner passageway 102 comprises an inner diameter of not less than about ½ inch.

Preferably, large-bore hand wand adapter 121 is provided to assist the medical practitioner in manipulating an attached suction adapter tip 101 during a medical procedure. Preferably, large-bore hand wand adapter 121 comprises a hand-graspable hollow cylindrical tube 140 that, in the present preferred embodiment, comprises an inner diameter larger than about ¼ inch but not exceeding the inner diameter of large bore inner passageway 102, as shown.

Preferably, large-bore hand wand adapter 121 comprises distal fluid-inlet 152, proximal fluid-outlet 154, and at least one large-bore inner-passageway 156 situate between such distal fluid-inlet 152 and such proximal fluid-outlet 154, as shown. Preferably, proximal fluid-outlet 154 comprises wand-outlet coupling 158 (at least embodying herein at least one third coupler) adapted to removably couple proximal fluid-outlet 154 to large-bore distal-end inlet-coupling 110' of the at least one large-bore suction conduit, as shown.

Preferably, distal fluid-inlet 152 comprises large-bore distal-end inlet-coupling 110" adapted to removably couple with a suction adapter tip 101 (or to other devices incorporating a compatible coupling members of large-bore medical suction system 100). Preferably, wand-outlet coupling 158, large-bore distal-end inlet-coupling 110" and large-bore distal-end inlet-coupling 110' are adapted to at least one medical coupler format. Most preferably, wand-outlet coupling 158, large-bore distal-end inlet-coupling 110" and large-bore distal-end inlet-coupling 110' are adapted to removably couple to 15 mm medical respiratory adapters and/or 22 mm medical respiratory adapters.

Preferably, large-bore hand wand adapter 121 comprises aperture valve 160 adapted to allow manual flow regulation of suction pressure. Preferably, aperture valve 160 (at least embodying herein at least one pressure regulator) comprises an aperture extending through outer wall 142 of hollow cylindrical tube 140 to allow a transfer of ambient fluid pressure to the interior of large-bore inner-passageway 156, as shown. During operation, aperture valve 160 acts as a pressure-relieving bypass to reduce the level of vacuum pressure within large-bore inner-passageway 156. In this state, the level of vacuum pressure at distal fluid-inlet 152 is limited. Applying a finger or thumb over aperture valve 160 blocks the transfer of ambient air into large-bore inner-passageway 156, thereby generating a state of increased vacuum pressure at distal fluid-inlet 152. Preferably, the level of vacuum pressure at distal fluid-inlet 152 is increased or decreased by varying the open area of aperture valve 160, preferably using thumb-controlled manipulation. In the present disclosure the term "thumb-controlled" shall included within the definition, any manual manipulation by any digit of a user's hand, or any portion of the user's hand. Preferably, aperture valve 160 is positioned away from distal fluid-inlet 152 to provide comfortable ergonomic gripping and to position the hand of the medical practitioner a safe distance from the teeth of the patient during oral suctioning.

Preferably, large-bore hand wand adapter 121 comprises at least one smooth angled bend 162, generally defining two non-congruent longitudinal axes, as shown. Providing a distal bend in the length of large-bore hand wand adapter 121 preferably provides the medical practitioner greater control of suction adapter tip 101 within a surgical field or the mouth, and provides greater access within the curve of the esophagus.

Preferably, large-bore hand wand adapter 121 comprises at least one substantially rigid material. Preferably, large-bore hand wand adapter 121 comprises at least one durable material allowing repeated sterilization between uses. More preferably, large-bore hand wand adapter 121 comprises at least one material suitable for single-use and disposal. Upon reading the teachings of this specification, those of ordinary skill in the art will now understand that, under appropriate circumstances, considering such issues as user preference, intended use, etc., other wand features, such as the application of grip-assisting outer surface treatments (ridges), forming portions of the wand from transparent materials to permit visualization of the aspirated material, incorporating integral hangers, tubing clips, user-assisting indicia, etc., may suffice.

Preferably, large bore medical suction system 100 comprises a set of interchangeable suction adapter tips 101 including narrow-bore suction component 111 and blunt tip suction component 116, as shown. Preferably, narrow-bore suction component 111 (at least embodying herein at least one narrow-bore passage) comprises a substantially flexible small-bore suction catheter 120 comprising large-bore adapter portion 112', as shown. Large-bore adapter portion 112' (at least embodying herein at least one first coupler) is preferably adapted to removably couple small-bore suction catheter 120 to large-bore distal-end inlet-coupling 110" of large-bore hand wand adapter 121 (as shown in FIG. 2), or to large-bore distal-end inlet-coupling 110' of large-bore suction conduit 125.

Preferably, blunt tip suction component 116 comprises a plurality of distal tip inlets 118 and a plurality of side inlets 119, as shown. Preferably, distal tip inlets 118 and side inlets 119 form a fine screen-like suction field identified herein as suction screen 130 (at least embodying herein at least one distal end tip screen). The preferred inlet pattern of the tip and sides of blunt tip suction component 116 allows fine atraumatic-suctioning of wide surface areas.

Blunt tip suction component 116 preferably comprises large-bore adapter portion 112", as shown (at least embodying herein at least one second coupler). Large-bore adapter portion 112" is preferably adapted to couple blunt tip suction component 116 to large-bore distal-end inlet-coupling 110" of large-bore hand wand adapter 121, or to large-bore distal-end inlet-coupling 110' of large-bore suction conduit 125. Upon reading the teachings of this specification, those of ordinary skill in the art will now understand that, under appropriate circumstances, considering such issues as user preference, intended use, etc., other suction adapter tip configurations, such as for other flow patterns, variable flow patterns, adjustable arrangements and functions, etc., may suffice.

Figure 3:
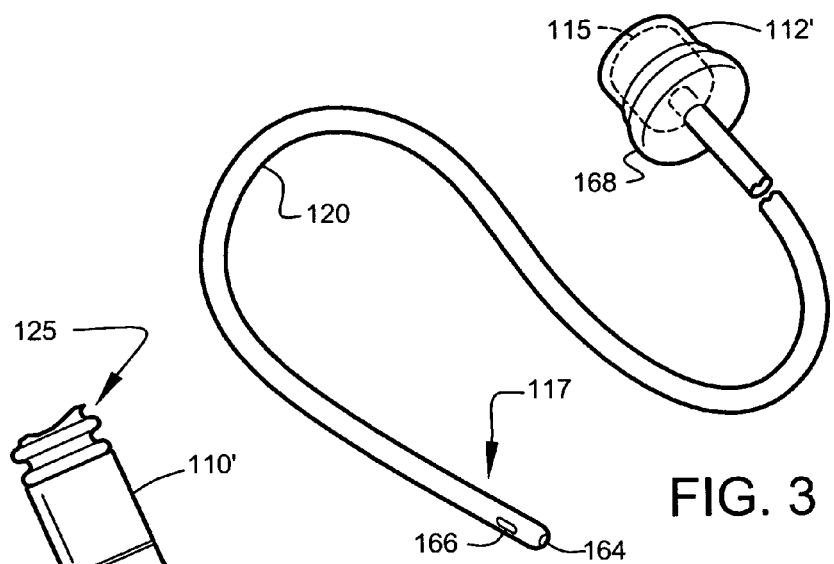
FIG. 3 shows an enlarged perspective view illustrating the narrow-bore suction component of FIG. 1.

FIG. 3 shows an enlarged perspective view illustrating narrow-bore suction component 111 of FIG. 1. Preferably, narrow-bore suction component 111 is structured and arranged for deep endotracheal tube tracheal suctioning. Preferably, narrow-bore suction component 111 comprises the properties of trachealbrochial suction catheters, including, having an appropriate inner and outer diameter, a sufficient length, and a sufficient flexibility to allow suctioning of the trachea and adjacent pulmonary structures, after insertion through an endotracheal tube of an intubated patient (see FIG. 4).

Preferably, narrow-bore suction component 111 comprises a long and substantially flexible tube (shown shortened for illustration purposes) identified herein as small-bore suction catheter 120. Preferably, small-bore suction catheter 120 comprises distal-end inlet segment 117 and proximal-end outlet 115, as shown. Preferably, distal-end inlet segment 117 comprises multiple inlets including distal tip inlet 164 and at least one safety relief inlet 166, preferably located within the sidewall of small-bore suction catheter 120, as shown.

Preferably, narrow-bore suction component 111 comprises large-bore adapter portion 112' coaxially situated about proximal-end outlet 115, as shown. Preferably, large-bore adapter portion 112' comprises proximal end inlet segment 168 having a substantially short length and substantially rigid stiffness. Since only proximal end inlet segment 168 is rigid and since small-bore suction catheter 120 is flexible, distal-end inlet segment 117 can be user positioned near proximal end inlet segment 168, reducing the overall length of the adapter, thus allowing narrow-bore suction component 111 to preferably function as a short adapter, if necessary or desired. Preferably, large-bore adapter portion 112' is adapted to removably couple to at least one vacuum source comprising at least one connection bore size of between about 10 mm and about 30 mm. Such vacuum sources preferably comprise at least one respiratory adapter comprising at least one bore size of between about 10 mm and about 30 mm, most preferably between about 15 mm and about 22 mm.

Figure 4:
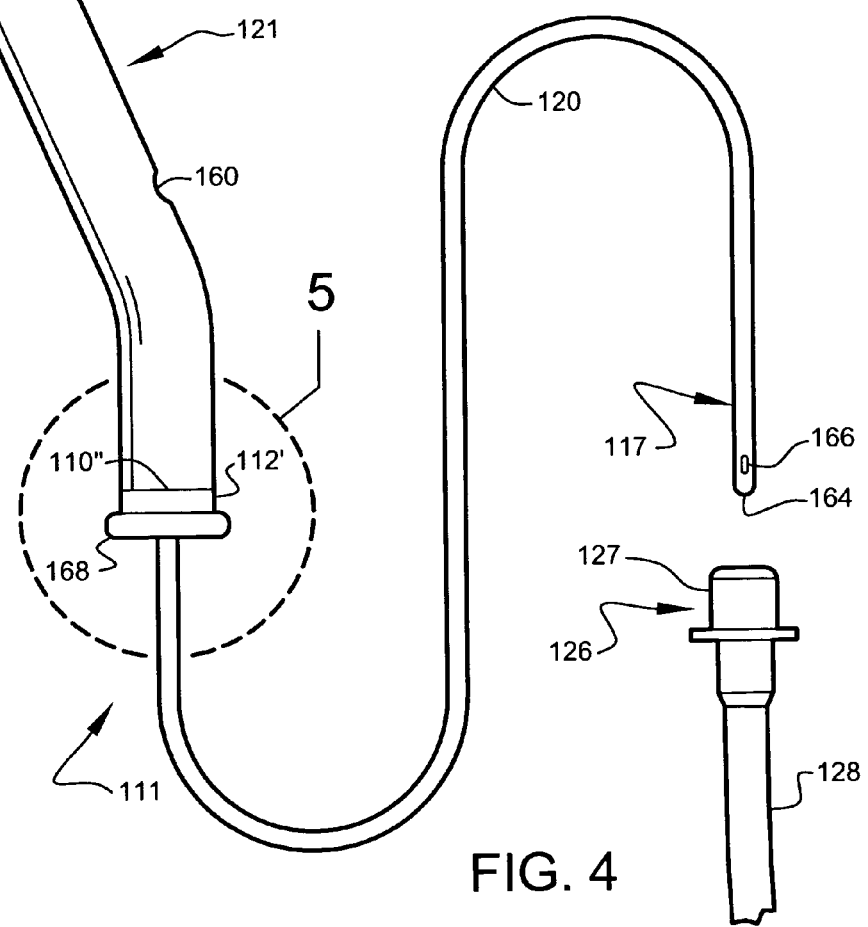
FIG. 4 shows a partial side view of the multipurpose large-bore medical suction system according to FIG. 2.

FIG. 4 shows a partial side view of multipurpose large-bore medical suction system 100 according to FIG. 2. In the illustration of FIG. 4, small-bore suction catheter 120 is shown positioned to enter endotracheal tube 126 (comprising endotracheal tube adapter 127 and tube portion 128) of a type used for patient intubation. Endotracheal tubes comprise inner diameters ranging from about 2.5 mm internal diameter (I.D.) to 10 mm I.D.

In FIG. 4, narrow-bore suction component 111 is coupled with distal fluid-inlet 152 of large-bore hand wand adapter 121. Preferably, large-bore hand wand adapter 121 is quickly adaptable to be used both for large bore suctioning (using blunt tip suction component 116) and for deep endotracheal tube suctioning using narrow-bore suction component 111, as shown.

Figure 8A:
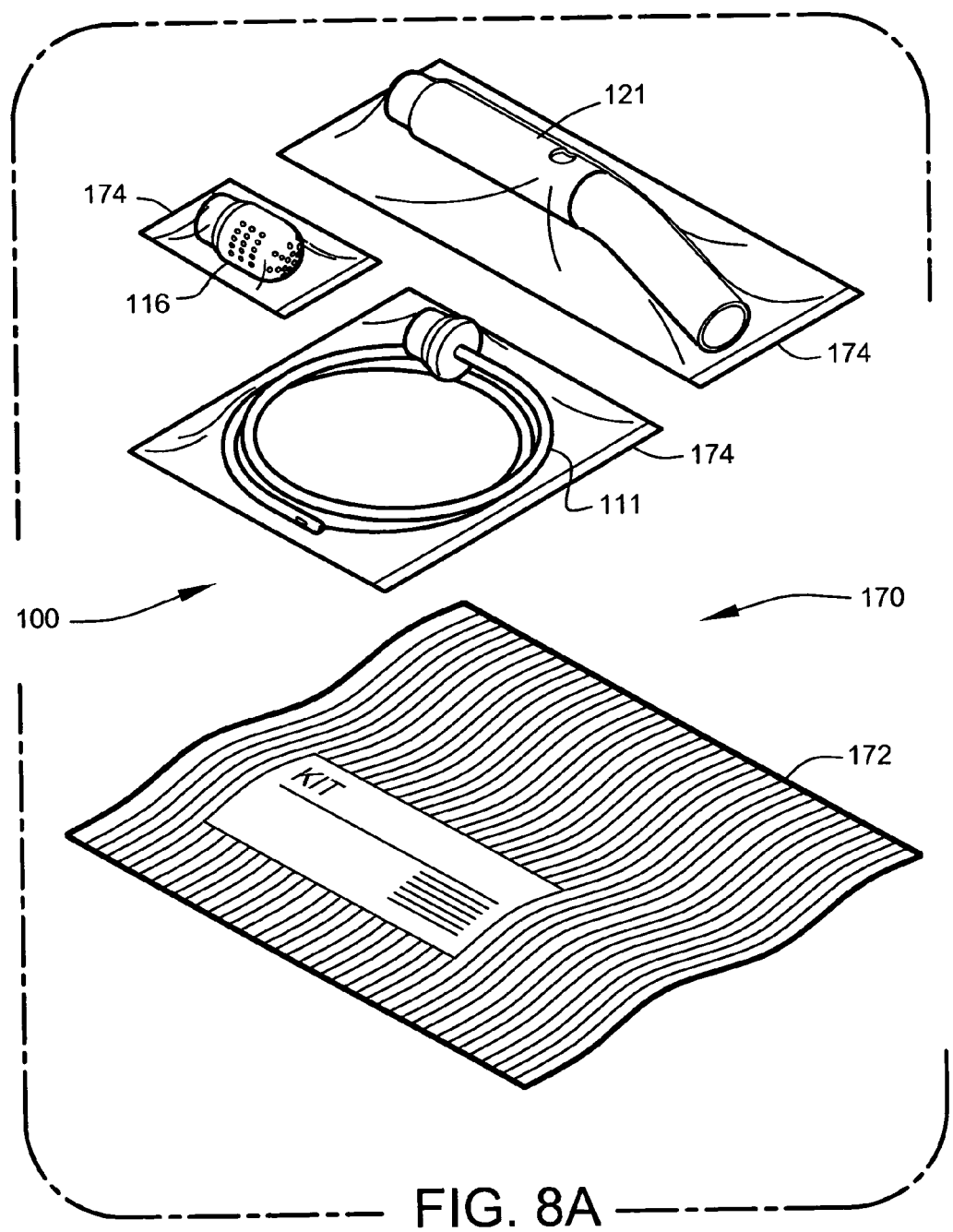
FIG. 8A shows a perspective view of a kit system comprising the multipurpose large-bore medical suction system, according to a preferred embodiment of the present invention.

Preferably, narrow-bore suction component 111 is included as a preferred component of the kit embodiments of large-bore medical suction system 100 (see FIG. 8A). In addition, narrow-bore suction component 111 is adapted to be used independently as a general narrow-bore aspirator, connectable to a large-bore medical vacuum source.

FIG. 5A shows a side view, in partial section, of narrow-bore suction component 111a coupled to large-bore hand wand adapter 121 of FIG. 1. Preferably, proximal-end outlet 115 of small-bore suction catheter 120 extends concentrically through the center portion of large-bore adapter portion 112', as shown. Preferably, the outer diameter of large-bore adapter portion 112' is standardized to provide a pressure-tight, removable, friction fit within distal-end inlet-coupling 110" of large-bore hand wand adapter 121, as shown. Large-bore adapter portion 112' preferably comprises either a "male" or "female" coupling member, most preferably a male coupling member, as shown. Preferably, the exiting internal passage of proximal-end outlet 115 enlarges in steps to provide one or more female-type coupling sockets 177, as shown, thus allowing for the coupling of smaller-diameter vacuum conduits and/or ports. For example, female-type coupling socket 177 is preferably adapted to additionally engage the narrow-bore vacuum ports 150 of medical collection canister 106 (this arrangement at least embodies herein wherein such at least one first coupler is adapted to removably couple to at least one first one and at least one second one of such at least one large-bore suction conduits; and such at least one first one comprises at least one end bore-diameter larger that that of such at least one second one).

Upon reading the teachings of this specification, those with ordinary skill in the art will now understand that, under appropriate circumstances, considering issues such as collection canister type, intended application, etc., other coupler format arrangements, such as, for example, adapting to both 15 millimeter (mm) and 22 millimeter (mm) medical conduit connections, adapting to custom coupler sizes, adapting to outlets having a diameter smaller than ¼ inch, etc., may suffice. Preferably, proximal end inlet segment 168 comprises a relatively short length to maintain maximum functionality and user control of large-bore hand wand adapter 121. Preferably, proximal end inlet segment 168 comprises a peripheral configuration adapted to assist in seating large-bore adapter portion 112' within large-bore hand wand adapter 121 and/or large-bore suction conduit 125.

Preferably, all coupling components of large-bore medical suction system 100 are adapted to form substantially pressure-tight seals when intercoupled. Preferably, all components of large-bore medical suction system 100 comprise either a "male" or "female" coupling member. Preferably, all coupling components of large-bore medical suction system 100 comprise smoothbore, tapered-friction coupling members. Upon reading the teachings of this specification, those of ordinary skill in the art will now understand that, under appropriate circumstances, considering such issues as user preference, intended use, etc., other coupling member arrangements, such as the use of locking mechanisms, including threads, helical threads, locks, bayonet fittings, interlocking designs, etc., may suffice.

FIG. 5B shows a side view, in partial section, of alternate narrow-bore suction component 111b coupled to distal inlet 103 of large-bore suction conduit 125. Preferably, alternate narrow-bore suction component 111b differs from narrow-bore suction component 111a by comprising a "stepped" set of male-type coupling adapters, as shown. Preferably, proximal-end outlet 115 of small-bore suction catheter 120 extends concentrically through the center portion of large-bore adapter portion 113, as shown. As with large-bore adapter portion 112', the outer diameter of large-bore adapter portion 113 is standardized to provide a pressure-tight, removable, friction fit within distal inlet 103 of large-bore suction conduit 125, as shown. Large-bore adapter portion 113 preferably comprises either a "male" or "female" coupling member, most preferably a male coupling member, as shown. Preferably, the outer diameter of adapter portion 113 is reduced in several steps to provide one or more additional male-type couplers 179, as shown. The preferred multi-diameter arrangement of adapter portion 113 allows alternate narrow-bore suction component 111b to be coupled to smaller-diameter vacuum ports and/or conduits (this arrangement at least embodies herein wherein such at least one first coupler is adapted to removably couple to at least one first one and at least one second one of such at least one large-bore suction conduits; and such at least one first one comprises at least one end bore-diameter larger that that of such at least one second one).

Upon reading the teachings of this specification, those with ordinary skill in the art will now understand that, under appropriate circumstances, considering issues such as collection canister type, intended application, etc., other coupler format arrangements, such as, for example, adapting to both 15 millimeter (mm) and 22 millimeter (mm) medical conduit connections, adapting to custom coupler sizes, adapting to outlets having a diameter smaller than ¼ inch, etc., may suffice. Furthermore, those with ordinary skill in the art, upon reading the teachings of this specification, will now understand that, under appropriate circumstances, considering issues such as, intended use, nature of medical procedure, etc., other adapter arrangements, such as, for example, adapting a large-bore adapter portion to allow for removal of a small-bore suction catheter, and replacement with other devices, such as Yankauer-type suction device, etc., may suffice.

FIG. 6 shows a perspective view illustrating blunt tip suction component 116 of large-bore medical suction system 100 according to a preferred embodiment of the present invention. Blunt tip suction component 116 preferably comprises large-bore adapter portion 112", as shown. Large-bore adapter portion 112" is preferably adapted to couple blunt tip suction component 116 to large-bore distal-end inlet-coupling 110" of large-bore hand wand adapter 121, or to large-bore distal-end inlet-coupling 110' of large-bore suction conduit 125.

Preferably, blunt tip suction component 116 comprises a plurality of narrow-bore inlets 122, specifically identified herein as distal tip inlets 118 and side inlets 119, as shown. Preferably, distal tip inlets 118 and side inlets 119 form a fine screen-like suction field identified herein as suction screen 130. The preferred inlet patterns on the distal tip and sides of blunt tip suction component 116 are adapted to provide atraumatic-suctioning of wide surface areas. Preferably, blunt tip suction component 116 comprises a number of narrow-bore inlets 122 at least greater than five, as shown. The preferred use of multiple "narrow bore" inlets at tip 123 provides greater user control within such a wide suctioning surface area. Since the illustrated arrangement of multiple "narrow bore" inlets preferably forms the preferred screen-like suction inlet (suction screen 130), large debris can be filtered while fine atraumatic suctioning capability is provided.

The preferred arrangement of multiple side inlets 119 forms a wide suctioning surface area that additionally functions to increase safety by preventing a locking of the vacuum system at high pressures, for example, if all distal tip inlets 118 were simultaneously blocked. This condition sometimes occurs during aspiration of shallow tissue-pockets within the surgical field. Removing a suction tip without breaking the suction increases the potential of tissue-ripping and related damage. This condition is potentially life threatening when the tissue comprises a bowel or critical blood vessel. Utilizing such preferred arrangement of narrow-bore inlets 122 of blunt tip suction component 116 reduces the potential for simultaneous occlusion of all the apertures and therefore eliminates the complications relating to unintentional tissue damage during aspiration.

FIG. 7 shows an end view illustrating preferred aperture patterns of large-bore blunt-tip component 116 of FIG. 6. The preferred "patterned" arrangement of suction screen 130 is clearly demonstrated in the end view FIG. 7. Preferred narrow-bore inlets 122 suitable for use with the present preferred embodiment, such as for fine atraumatic suctioning adjacent delicate body tissues, preferably range in diameter from about 0.5 mm to about 5 mm, as shown. Upon reading the teachings of this specification, those with ordinary skill in the art will now understand that, under appropriate circumstances, considering issues such as type of material to be aspirated, filtering requirements, etc., other inlet arrangements, such as, for example, using larger or smaller inlet apertures, providing secondary filtering materials, providing alternate aperture patterns to enhance specific suction flow characteristics, etc., may suffice.

FIG. 8A shows a perspective view of kit system 170 comprising multipurpose large-bore medical suction system 100, according to a preferred embodiment of the present invention. Preferably, kit system 170, as illustrated in FIG. 8A, is designed primarily (but not exclusively) for use by a medical practitioner, such as a doctor, for rendering medical treatment to a patient or other person under emergency conditions. Kit system 170 is also useful for use by non-professionals, such as a medical caregiver, to assist in endotracheal tube tracheal suctioning in a home setting.

One preferred embodiment of kit system 170 generally comprises narrow-bore suction component 111, blunt tip suction component 116, large-bore hand wand adapter 121, and package 172, as shown. Package 172 preferably comprises a sealable plastic bag, as shown. Preferably, kit system 170 is formed by sealing narrow-bore suction component 111, blunt tip suction component 116, and large-bore hand wand adapter 121 within package 172. Most preferably, narrow-bore suction component 111 (at least embodying herein at least one narrow-bore tracheal suction catheter), blunt tip suction component 116, and large-bore hand wand adapter 121 are each sealed within individual sterile packages 174, as shown, prior to assemblage within package 172. Upon reading the teachings of this specification, those with ordinary skill in the art will now understand that, under appropriate circumstances, considering issues such as intended use, cost, etc., other packaging arrangements, such as, for example, providing a single package comprising a blow-molded tray, including labeling and instructions for use, etc., may suffice.

Figure 8B:
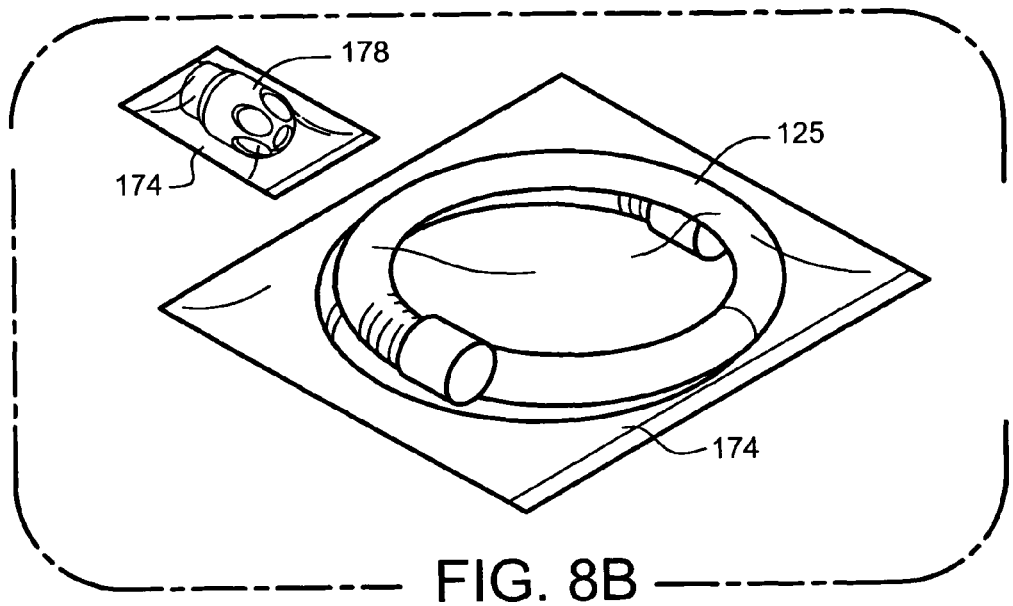
FIG. 8B shows a perspective view of additional components of the kit system, according to another preferred embodiment of the present invention.

FIG. 8B shows a perspective view of additional components of kit system 170, according to an additional preferred embodiment of the present invention. Preferably, the specific contents of preferred embodiments of kit system 170 are adjustable to accommodate the requirements of a specific treatments or medical procedures. Thus, a cardiopulmonary resuscitation kit, an oropharyngeal trauma kit, and a toxic ingestion kit preferably comprise procedure-specific selections of system components.

As a representative example, a preferred embodiment of kit system 170 preferably comprises one or both of the additional system components of FIG. 8B, as shown. More specifically, preferred embodiment of kit system 170 preferably comprises alternate blunt tip adapter 178 and/or large-bore suction conduit 125, as shown.

Figure 9:
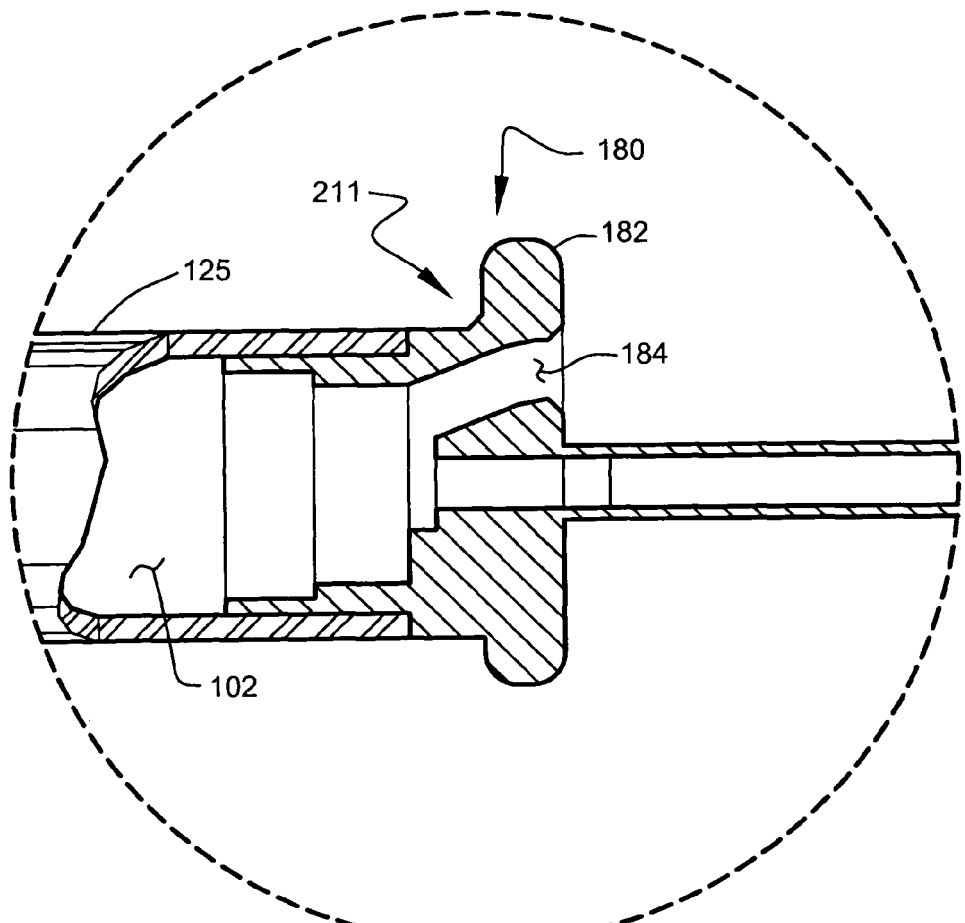
FIG. 9 shows a side view, in partial section, of a narrow-bore suction component, comprising a valve aperture, coupled to the large-bore hand wand of FIG. 2.

FIG. 9 shows a side view, in partial section, of narrow-bore suction component 211, comprising valve aperture, coupled to the large-bore hand wand of FIG. 2. Preferably, narrow-bore suction component 211 comprises large-bore adapter portion 182 (substantially similar in configuration to large-bore adapter portion 112' of FIG. 5) modified to comprise valve aperture 184, as shown. Preferably, valve aperture 184 is adapted to allow finger flow regulation of suction pressure. Preferably, valve aperture 184 comprises an aperture extending through large-bore adapter portion 182 of narrow-bore suction component 211 to allow a transfer of ambient fluid pressure to the interior of ambient to large bore inner passageway 102 of large-bore suction conduit 125, as shown. During operation, valve aperture 186 acts as a pressure-relieving bypass allowing user modulation of the level of vacuum pressure within large bore inner passageway 102.

FIG. 10 shows perspective views of alternate suction wand 200 comprising rotatable vacuum modulator 202 according to preferred embodiment of the present invention. Preferably, alternate suction wand 200 is similar to large-bore hand-wand adapter 121 in assisting the medical practitioner in manipulating an attached suction adapter tip during a medical procedure. Preferably, alternate suction wand 200 comprises a hand-graspable hollow cylindrical tube 240 that, in the present preferred embodiment, comprises an inner diameter larger than about ¼ inch but not exceeding the inner diameter of large bore inner passageway 102 (as described above).

Preferably, alternate suction wand 200 comprises distal fluid-inlet 252, proximal fluid-outlet 254, and at least one large-bore inner-passageway 256 situate between such distal fluid-inlet 252 and such proximal fluid-outlet 254, as shown. Preferably, proximal fluid-outlet 254 comprises wand-outlet coupling 258 (at least embodying herein at least one third coupler and at least embodying herein at least one wand-outlet coupler) adapted to removably couple proximal fluid-outlet 254 to large-bore distal-end inlet-coupling 110' of the at least one large-bore suction conduit (see FIG. 1).

Preferably, distal fluid-inlet 252 comprises large-bore distal-end inlet-coupling 210 adapted to removably couple with a suction adapter tip 101 (or to other devices incorporating a compatible coupling members of large-bore medical suction system 100). Preferably, wand-outlet coupling 258, large-bore distal-end inlet-coupling 210 and large-bore distal-end inlet-coupling 110' are adapted to at least one medical coupler format. Most preferably, wand-outlet coupling 258, large-bore distal-end inlet-coupling 210 and large-bore distal-end inlet-coupling 110' are adapted to removably couple to 15 mm medical respiratory adapters and/or 22 mm medical respiratory adapters.

Preferably, alternate suction wand 200 comprises a rotatable vacuum modulator 202 adapted to allow manual flow regulation of suction pressure. Preferably, vacuum modulator 202 (at least embodying herein at least one pressure regulator) comprises at least one aperture; preferably, two apertures identified herein as aperture 204 and aperture 206, as shown (at least embodying herein at least one first aperture).

Preferably, aperture 204 and aperture 206 extend through outer wall 242 of hollow cylindrical tube 240 to allow a transfer of ambient fluid pressure to the interior of large-bore inner-passageway 256, as shown. Vacuum modulator 202 further preferably comprises rotatable ring 208, as shown. Preferably, rotatable ring 208 (at least embodying herein at least such at least one adjustable occluder) comprises a hollow cylindrical ring coaxially disposed about hollow cylindrical tube 240, as shown. Preferably, rotatable ring 208 is located over aperture 204 and aperture 206, preferably adjacent distal fluid-inlet 252, as shown.

Rotatable ring 208 preferably comprises a corresponding set of apertures identified herein as aperture 212 and aperture 214 (see also FIG. 11). Preferably, both aperture 212 and aperture 214 (at least embodying herein at least one second aperture) are sized and positioned to be alignable, by rotation of rotatable ring 208, with aperture 204 and aperture 206, as shown.

FIG. 11 shows a partial side view, of a cut-away section, of alternate suction wand 200 of FIG. 10 in a standby configuration. FIG. 12 shows a partial side view, of a cut-away section, of alternate suction wand 200 in a suctioning configuration. Rotatable ring 208 is preferably adapted to adjustably occlude (block) aperture 204 and aperture 206 between a fully open aperture state (as illustrated in FIG. 11) and fully closed aperture state (as illustrated in FIG. 12). Such adjusting of rotatable ring 208 is preferably controllable by the user, preferably by manual rotation.

During operation, aperture 204 and aperture 206 are either blocked (occluded) by the solid portions of rotatable ring 208, or are partially or fully open by rotational alignment of aperture 212 and aperture 214. When un-blocked, aperture 204 and aperture 206 each act as pressure-relieving bypass to reduce the level of vacuum pressure within large-bore inner-passageway 256. In such a "standby" state, as illustrated in FIG. 11, the level of vacuum pressure at distal fluid-inlet 252 is limited. Misaligning the apertures by turning rotatable ring 208 preferably blocks the transfer of ambient air 216 into large-bore inner-passageway 256, thereby generating a state of increased vacuum pressure at distal fluid-inlet 252 (as illustrated in FIG. 12). Preferably, the level of vacuum pressure at distal fluid-inlet 252 is increased or decreased by varying the open aperture area, preferably using thumb-controlled manipulation. In the present disclosure the term "thumb-controlled" shall included within the definition, any manual manipulation by any digit of a user's hand, or any portion of the user's hand.

Preferably, alternate suction wand 200 comprises at least one smooth angled bend 262, generally defining two non-congruent longitudinal axes, and comprises at least one substantially rigid material.

Figure 13:
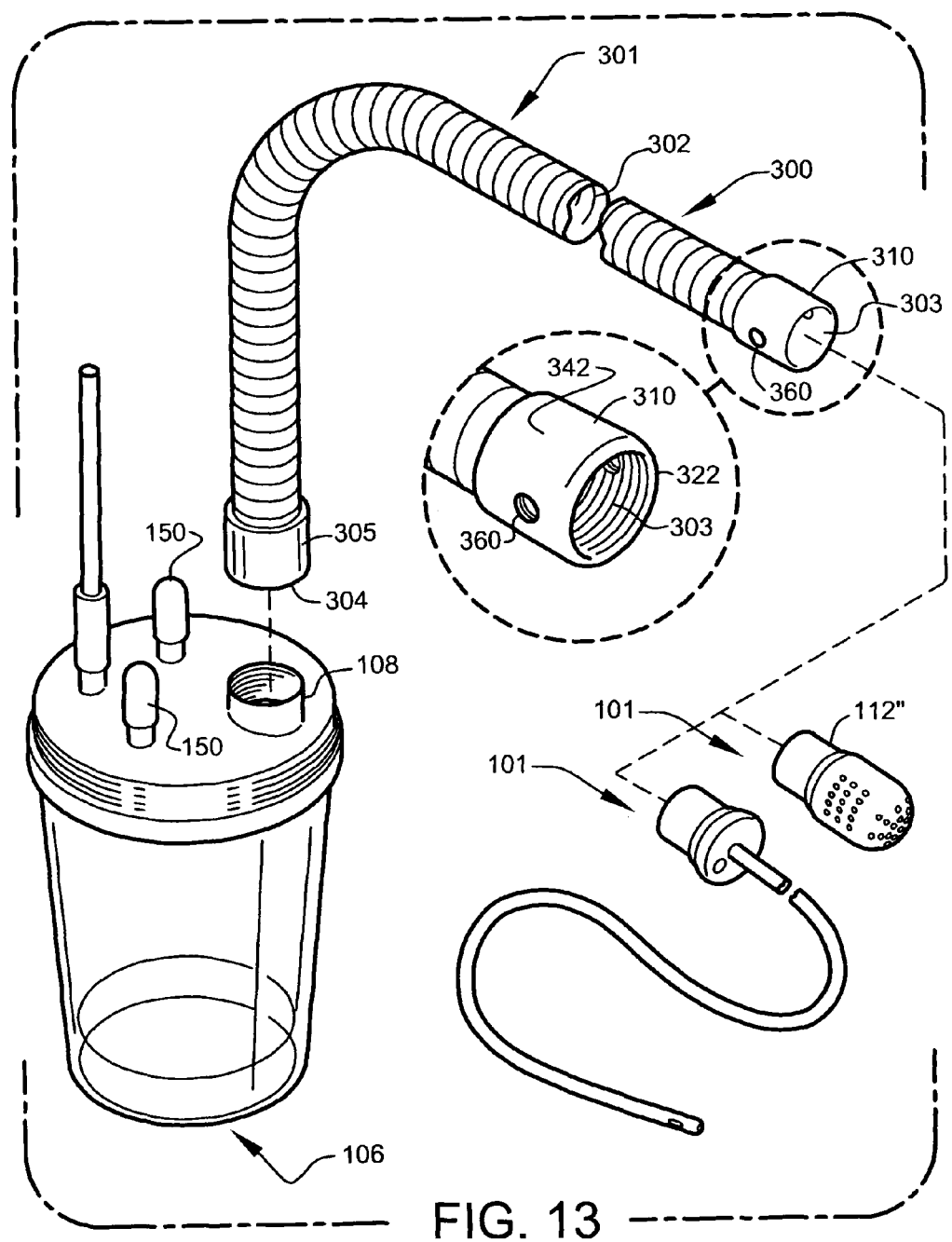
FIG. 13 shows a perspective view illustrating an alternate multipurpose large-bore medical suction system according to a preferred embodiment of the present invention.

FIG. 13 shows a perspective view illustrating alternate multipurpose large-bore medical suction system 300 according to a preferred embodiment of the present invention. Alternate multipurpose large-bore medical suction system 300 is preferably adapted to be directly usable as a medical suction device, suitable for vacuum-controllable atraumatic suctioning of a surgical field. In addition, alternate multipurpose large-bore medical suction system 300 is preferably adapted for use as a large-bore suction conduit usable in combination with various suction adapter tips 101, as shown. This highly preferred arrangement allows the medical practitioner to perform rapid removal of fluids from a surgical field, through direct use of alternate multipurpose large-bore medical suction system 300, and refined (treatment specific) suctioning procedures, by attaching a suitable suction adapter tip 101, as shown.

Preferably, alternate multipurpose large-bore medical suction system 300 of large bore medical suction system 100 comprises a specially designed suction conduit 301, as shown. Preferably, suction conduit 301 comprises large bore inner passageway 302 (at least embodying herein at least one fluid channel) situate between distal inlet 303 and proximal outlet 304, as shown. Preferably, suction conduit 301 of alternate multipurpose large-bore medical suction system 300 further comprises large-bore proximal-end outlet-coupling 305 (at least embodying herein at least one tip coupler) adapted to form an airtight coupling seal with large-bore inlet opening 108, as shown. The opposing end of suction conduit 301 preferably comprises large-bore distal-end inlet-coupling 310, as shown.

Preferably, large-bore distal-end inlet-coupling 310 comprises at least one aperture valve 360 adapted to allow manual flow regulation of suction pressure (at least embodying herein wherein such at least one fluid channel comprises at least one pressure-regulating aperture adapted to assist in providing pressure regulation of at least one level of fluid pressure within such at least one fluid channel). Preferably, aperture valve 360 (at least embodying herein at least one pressure regulator) comprises an aperture extending through outer wall 342 of large-bore distal-end inlet-coupling 310 to allow a transfer of ambient fluid pressure to the interior of large-bore inner passageway 302, as shown. Preferably, large-bore distal-end inlet coupling 310 of alternate multipurpose large-bore medical suction system 300 is physically configured to removably connect with 15 mm respiratory coupling members and/or 22 mm respiratory coupling members. Upon reading the teachings of this specification, those of ordinary skill in the art will now understand that, under appropriate circumstances, considering such issues as user preference, intended use, etc., other connector formats, such as proprietary configurations, instrument specific adapters, alternate handing of male and female connector ends, etc., may suffice.

Preferably, the inner diameter of large bore inner passageway 302 comprises a measurement that is not less than about ¼ inch. More preferably, large bore inner passageway 302 comprises an inner diameter of not less than about ½ inch.

FIG. 14 shows a side view illustrating alternate large-bore medical suction system 300, in use, according to the preferred embodiment of FIG. 13. Preferably, alternate large-bore medical suction system 300 is adapted to be hand graspable during use, as shown. Preferably, as illustrated in FIG. 14, the circumferential periphery 322 of distal inlet 303 comprises a substantially smooth and rounded shape to prevent damage to delicate tissues of the surgical field. In addition, circumferential periphery 322 of distal inlet 303 preferably comprises a substantially soft and resilient material selected to further reduce tissue trauma during use (at least embodying herein wherein such at least one tip coupler comprises at least one atraumatic shape adapted to reduce tissue trauma during at least one medical suctioning procedure using such at least one tip coupler; and such at least one atraumatic shape comprises at least one substantially rounded surface and at least embodying herein wherein such at least one tip coupler comprises at least one substantially resilient material adapted to reduce tissue trauma during at least one medical suctioning procedure using such at least one tip coupler). Materials suitable for use in the construction of large-bore distal-end inlet-coupling 310 include medical-grade silicones.

During operation, aperture valve 360 acts as a pressure-relieving bypass to reduce the level of vacuum pressure within large-bore inner passageway 302. In this state, the level of vacuum pressure at distal inlet 303 is limited. Applying a finger or thumb 309 over aperture valve 360 blocks the transfer of ambient air into large-bore inner passageway 302, thereby generating a state of increased vacuum pressure at distal inlet 303. Preferably, the level of vacuum pressure at distal inlet 303 is increased or decreased by varying the open area of aperture valve 360, preferably using thumb-controlled manipulation.

FIG. 15 shows a sectional view through the section 15-15 of FIG. 14 illustrating alternate multipurpose large-bore medical suction system 300 without an installed tip. FIG. 15 shows a sectional view aligned with section 15-15 of FIG. 14 illustrating alternate multipurpose large-bore medical suction system 300 with suction adapter tip 101 installed. Preferably, large-bore distal-end inlet-coupling 310 is adapted such that aperture valve 360 is substantially occluded, most preferably fully occluded with suction adapter tip 101 installed (at least embodying herein wherein such at least one distal inlet comprises at least one tip coupler adapted to couple at least one medical tip device to such at least one distal inlet; and such at least one pressure-regulating aperture is structured and arranged to be substantially occluded by such coupling of such at least one medical tip device to such at least one tip coupler). This allows manual vacuum control of alternate multipurpose large-bore medical suction system 300 to be transferred from large-bore distal-end inlet-coupling 310 to the pressure modulation device included with suction adapter tip 101. For example, coupling large-bore hand-wand adapter 121 of FIG. 1 to large-bore distal-end inlet-coupling 310 of alternate multipurpose large-bore medical suction system 300 effectively blocks aperture valve 360 thus shifting vacuum control from aperture valve 360 to aperture valve 160 of large-bore hand-wand adapter 121 (see FIG. 1).

Figure 17:
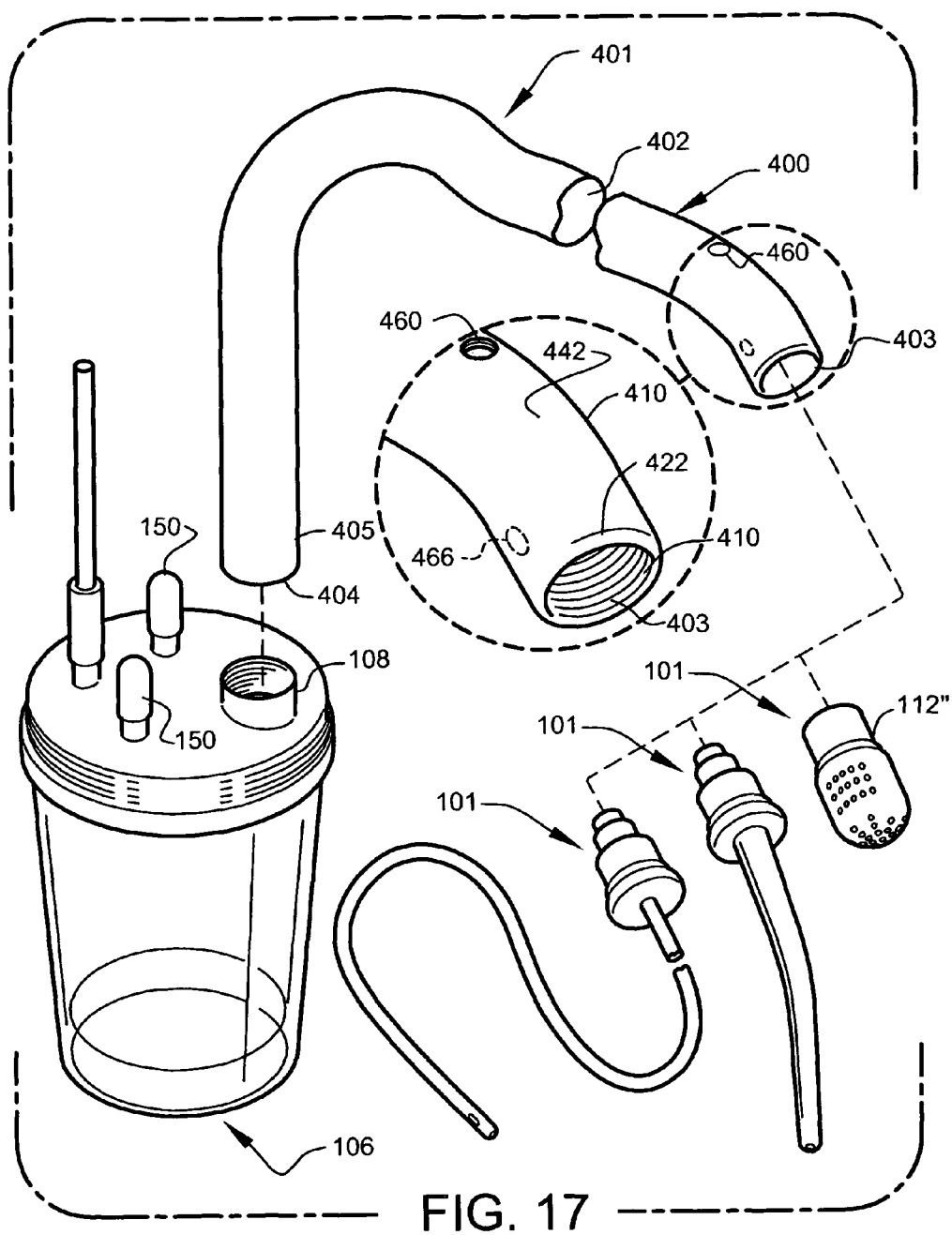
FIG. 17 shows a perspective view illustrating an alternate multipurpose large-bore medical suction system according to another preferred embodiment of the present invention.

FIG. 17 shows a perspective view illustrating alternate multipurpose large-bore medical suction system 400 according to another preferred embodiment of the present invention. Alternate multipurpose large-bore medical suction system 400 is preferably adapted to be directly usable as a medical suction device, suitable for vacuum-controllable atraumatic suctioning of a surgical field. In addition, alternate multipurpose large-bore medical suction system 400 is preferably adapted for use as a large-bore suction conduit, in combination with various suction adapter tips 101, as shown. This highly preferred arrangement allows the medical practitioner to perform rapid removal of fluids from a surgical field, through direct use of alternate multipurpose large-bore medical suction system 400, and refined (treatment specific) suctioning procedures, by attaching a suitable suction adapter tip 101, as shown. Preferred suction adapter tips 101 include Yankauer-type suction tips, large-bore suction tips, and flexible small-bore suction catheters, as shown.

Preferably, alternate multipurpose large-bore medical suction system 400 of large bore medical suction system 100 comprises a substantially flexible suction conduit 401, as shown. Preferably, suction conduit 301 comprises large bore inner passageway 402 (at least embodying herein at least one fluid channel) situate between distal inlet 403 and proximal outlet 404, as shown. Preferably, the inner diameter of large bore inner passageway 402 comprises a measurement that is not less than about ¼ inch. More preferably, large bore inner passageway 402 comprises an inner diameter of not less than about ½ inch.

Preferably, suction conduit 401 of alternate multipurpose large-bore medical suction system 400 further comprises large-bore proximal-end outlet-coupling 405 adapted to form an airtight coupling seal with large-bore inlet opening 108, as shown. The opposing end of suction conduit 401 preferably comprises large-bore distal-end inlet-coupling 410, as shown. Preferably, large-bore distal-end inlet coupling 410 (at least embodying herein at least one tip coupler) of alternate multipurpose large-bore medical suction system 400 is physically configured to removably connect with 15 mm respiratory coupling members and/or 22 mm respiratory coupling members.

Preferably, suction conduit 401 comprises at least one aperture valve 460 adapted to allow manual flow regulation of suction pressure (at least embodying herein wherein such at least one fluid channel comprises at least one pressure-regulating aperture adapted to assist in providing pressure regulation of at least one level of fluid pressure within such at least one fluid channel). Preferably, aperture valve 460 (at least embodying herein at least one pressure regulator) comprises an aperture extending through outer wall 442 of suction conduit 401 to allow a transfer of ambient fluid pressure to the interior of large-bore inner passageway 402, as shown. Upon reading the teachings of this specification, those of ordinary skill in the art will now understand that, under appropriate circumstances, considering such issues as user preference, intended use, etc., other connector formats, such as proprietary configurations, instrument specific adapters, alternate handing of male and female connector ends, etc., may suffice. Preferably, aperture valve 460 is situated between about one inches and about eighteen inches from distal inlet 403 to allow comfortable finger manipulation of aperture valve 460. During preferred operation, aperture valve 460 acts as a pressure-relieving bypass to reduce the level of vacuum pressure within large-bore inner passageway 402. In this state, the level of vacuum pressure at distal inlet 403 is limited. Applying a finger or thumb over aperture valve 460 blocks the transfer of ambient air into large-bore inner passageway 402, thereby generating a state of increased vacuum pressure at distal inlet 403. Preferably, the level of vacuum pressure at distal inlet 403 is increased or decreased by varying the open area of aperture valve 460, preferably using thumb/finger-controlled manipulation.

Preferably, suction conduit 401 is substantially flexible along its length. More preferably, suction conduit 401 is substantially flexible at least adjacent distal inlet 403, as shown. Preferably, the circumferential periphery 422 of distal inlet 403 comprises a substantially smooth and rounded shape to prevent damage to delicate tissues of the surgical field. In addition, circumferential periphery 422 of distal inlet 403 preferably comprises a substantially soft and resilient material selected to further reduce tissue trauma during use (at least embodying herein wherein such at least one distal inlet comprises at least one atraumatic shape adapted to reduce tissue trauma during at least one medical suctioning procedure; and such at least one atraumatic shape comprises at least one substantially rounded surface and at least embodying herein wherein such at least one distal inlet comprises at least one substantially resilient material adapted to reduce tissue trauma during at least one medical suctioning procedure). Materials suitable for use in the construction of distal inlet 403 include medical-grade silicones, Poly Vinyl Chlorides (PVC), and Urethanes. Materials preferred for use in the construction of distal inlet 403 (and/or distal portions of suction conduit 401) are substantially transparent.

Preferably, suction conduit 401 optionally comprises at least one safety relief inlet 466, preferably extending through outer wall 442 of suction conduit 401, as shown. This preferred option further assists in reducing tissue trauma during medical suctioning procedures by allowing a small but steady transfer of ambient fluid pressure to the interior of large-bore inner passageway 402, thus restricting suction pressure at distal inlet 403 to a predetermined level.

Although applicant has described applicant's preferred embodiments of this invention, it will be understood that the broadest scope of this invention includes modifications such as diverse shapes, sizes, and materials. Such scope is limited only by the below claims as read in connection with the above specification.

Further, many other advantages of applicant's invention will be apparent to those skilled in the art from the above descriptions and the below claims.

What is claimed is:

1. A system relating to multipurpose large-bore medical suction systems, compatible with at least one large-bore suction conduit comprising at least one distal inlet and at least one proximal outlet, wherein such at least one proximal outlet is connectable to at least one large-bore port of at least one collection canister, wherein such at least one distal inlet comprises at least one large inlet-bore-diameter no larger than about the large inlet-bore-diameter of the at least one large-bore port, and wherein such at least one distal inlet is adapted to allow fluid communication with such at least one large-bore port, said system comprising:
    a) at least one narrow-bore suction component adapted to pass at least one pressurized fluid; and
    b) at least one large-bore adapter structured and arranged to adapt said at least one narrow-bore suction component to the at least one distal inlet of the at least one large-bore suction conduit;
    c) wherein said at least one narrow-bore suction component comprises at least one substantially flexible conduit portion adapted to provide independent flexible conduit positioning of said at least one narrow-bore suction component.

2. The system according to claim 1 wherein said at least one narrow-bore suction component comprises a sufficient length and flexibility to allow entry of said at least one narrow-bore suction component into at least one endotracheal tube to allow tracheal suctioning; wherein said sufficient flexibility permits said at least one narrow-bore suction component to contour the at least one endotracheal tube.

3. The system according to claim 1 wherein said at least one narrow-bore suction component comprises at least one narrow-bore tracheal suction catheter adapted to assist deep endotracheal tube tracheal suctioning.

4. The system according to claim 1 wherein:
    a) said at least one large-bore adapter comprises at least one first coupler adapted to removably couple said at least one narrow-bore suction component to the at least one distal inlet of the at least one large-bore suction conduit; and
    b) said at least one first coupler is structured and arranged to form at least one pressure-resisting seal with such at least one distal inlet.

5. The system according to claim 4 wherein:
    a) said at least one first coupler is adapted to removably couple to at least one first one and at least one second one of such at least one large-bore suction conduits; and
    b) such at least one first one comprises at least one end bore-diameter larger that that of such at least one second one.

6. The system according to claim 4 wherein such at least one large-bore suction conduit comprises at least one bore-diameter larger than about ¼ inch.

7. The system according to claim 4 wherein said at least one first coupler is adapted to removably couple to at least one vacuum source comprising at least one about-15 millimeter-diameter coupling member.

8. The system according to claim 4 wherein said at least one first coupler is adapted to removably couple to at least one vacuum source comprising at least one about-22 millimeter-diameter coupling member.

9. The system according to claim 1 further comprising such at least one large-bore suction conduit.

10. The system according to claim 9 wherein:
    a) said at least one large-bore suction conduit comprises at least one distal inlet and at least one proximal outlet;
    b) said at least one proximal outlet is adapted to couple to the at least one large-bore port of the at least one collection canister;
    c) wherein said at least one distal inlet comprises at least one large inlet-bore-diameter substantially matching the inlet bore-diameter of the at least one large-bore port; and
    d) wherein said at least one proximal outlet is structured and arranged to allow fluid communication between such at least one large-bore port and said at least one distal inlet.

11. A system relating to multipurpose large-bore medical suction systems connectable to at least one large-bore port of at least one medical collection canister comprising:
    a) at least one substantially flexible large-bore suction conduit comprising
        i) at least one distal inlet,
        ii) at least one proximal outlet, and
        iii) at least one substantially flexible fluid channel adapted to channel at least one fluid between said at least one distal inlet and said at least one proximal outlet;
    b) wherein said at least one proximal outlet is connectable to the at least one large-bore port of the at least one medical collection canister; and
    c) wherein said at least one fluid channel comprises at least one pressure-regulating aperture adapted to assist in providing pressure regulation of at least one level of fluid pressure within said at least one fluid channel.

12. The system according to claim 11 wherein said at least one distal inlet comprises at least one bore diameter larger than about ¼ inch.

13. The system according to claim 11 wherein said at least one pressure-regulating aperture is structured and arranged to be manually operable by at least one hand of at least one user.

14. The system according to claim 11 wherein a distal portion of said at least one large-bore suction conduit is flexible.

15. The system according to claim 14 wherein said at least one pressure-regulating aperture is positioned closer to said distal portion than to said at least one proximal outlet.

* * * * *